(12) United States Patent
Palmer et al.

(10) Patent No.: US 10,105,706 B2
(45) Date of Patent: Oct. 23, 2018

(54) CONTAINER ASSEMBLY AND SYSTEM FOR DETECTION THEREOF

(75) Inventors: Ashley Palmer, Englewood, NJ (US); Kurt Stoeckmann, Madison, NJ (US); Craig Owen Russ, Wayne, NJ (US); Robert S. Ross, White Plains, NY (US); Girish Parmar, Easton, PA (US); Craig A. Gelfand, Jackson, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/009,337

(22) Filed: Jan. 19, 2011

(65) Prior Publication Data

US 2011/0311416 A1    Dec. 22, 2011

Related U.S. Application Data

(60) Provisional application No. 61/415,631, filed on Nov. 19, 2010, provisional application No. 61/296,437, filed on Jan. 19, 2010.

(51) Int. Cl.
  *B01L 3/00* (2006.01)
  *A61B 10/00* (2006.01)
  *G01N 21/64* (2006.01)

(52) U.S. Cl.
  CPC ............ *B01L 3/5457* (2013.01); *B01L 3/50* (2013.01); *B01L 3/5453* (2013.01);
  (Continued)

(58) Field of Classification Search
  CPC . B01L 3/50; B01L 3/505; B01L 3/508; G01N 21/64
  (Continued)

(56) References Cited

U.S. PATENT DOCUMENTS

| 3,829,690 A | * | 8/1974 | Snyder | ............... G01N 21/9054 250/302 |
| 4,140,631 A | | 2/1979 | Okuda et al. | |

(Continued)

FOREIGN PATENT DOCUMENTS

| EP | 0384331 A2 | 8/1990 |
| EP | 1005909 A2 | 6/2000 |

(Continued)

OTHER PUBLICATIONS

Portions of product literature catalog commercially available from Greiner Bio One at www.gbo.com/documents/980042_VACUETTEkatalog_rev04_0609_small_e.pdf.

(Continued)

*Primary Examiner* — Dennis White
*Assistant Examiner* — Bryan Kilpatrick
(74) *Attorney, Agent, or Firm* — The Webb Law Firm

(57) ABSTRACT

A closure and a container assembly are disclosed. The closure includes a first visual identifier and a second visual identifier, wherein the second visual identifier is different from the first visual identifier. The first visual identifier may be a first color, and the second visual identifier may be a second color. At least one of the first and/or second visual identifier may include a fluorescent compound having a characteristic fluorescent spectra. The first visual identifier and the second visual identifier may be provided on the annular skirt of the closure. The fluorescent compound may be provided on at least one of the closure and the container assembly and can be used to facilitate automated visualization of the fluorescent compound under fluorescence excitation light.

5 Claims, 32 Drawing Sheets

(52) U.S. Cl.
CPC ......... *A61B 10/0096* (2013.01); *B01L 3/5082* (2013.01); *B01L 2200/12* (2013.01); *B01L 2300/021* (2013.01); *B01L 2300/046* (2013.01); *G01N 21/64* (2013.01)

(58) Field of Classification Search
USPC ............ 422/547, 82.08, 558; 206/459–459.9
See application file for complete search history.

(56) References Cited

U.S. PATENT DOCUMENTS

| | | | |
|---|---|---|---|
| 4,141,654 A | | 2/1979 | Wardlaw et al. |
| 4,770,779 A | | 9/1988 | Ichikawa et al. |
| 4,919,855 A | * | 4/1990 | Thomas ............... A43B 3/0084 264/21 |
| 4,946,601 A | | 8/1990 | Fiehler |
| 5,254,314 A | | 10/1993 | Yu et al. |
| 5,461,136 A | * | 10/1995 | Krutak et al. ................. 528/289 |
| 5,585,247 A | * | 12/1996 | Habenstein ..................... 435/18 |
| 5,605,230 A | * | 2/1997 | Marino et al. ................ 206/534 |
| 6,225,123 B1 | | 5/2001 | Cohen et al. |
| 6,277,331 B1 | * | 8/2001 | Konrad ........................... 422/547 |
| 6,280,400 B1 | | 8/2001 | Niermann |
| 6,406,671 B1 | | 6/2002 | DiCesare et al. |
| 6,426,049 B1 | | 7/2002 | Rosen et al. |
| 6,562,300 B2 | | 5/2003 | Rosen et al. |
| 6,602,206 B1 | | 8/2003 | Niermann et al. |
| 6,612,997 B1 | | 9/2003 | Hutton |
| 6,749,078 B2 | | 6/2004 | Iskra |
| 6,821,789 B2 | | 11/2004 | Augello et al. |
| 6,910,597 B2 | | 6/2005 | Iskra |
| 7,309,468 B2 | | 12/2007 | Stevens et al. |
| 7,323,889 B2 | | 1/2008 | Pfaff et al. |
| 2004/0150217 A1 | | 8/2004 | Heffelfinger et al. |
| 2004/0263843 A1 | * | 12/2004 | Knopp et al. ................. 356/301 |
| 2005/0194280 A1 | * | 9/2005 | Smith ........................ 206/459.5 |
| 2006/0177352 A1 | | 8/2006 | Ziegmann et al. |

FOREIGN PATENT DOCUMENTS

| | | |
|---|---|---|
| EP | 1006359 A2 | 6/2000 |
| EP | 1006360 A2 | 6/2000 |
| EP | 1014088 A2 | 6/2000 |
| EP | 1106253 A2 | 6/2001 |
| EP | 2111795 A1 | 10/2009 |
| FR | 2858852 A1 | 2/2005 |
| FR | 2861702 A1 | 5/2005 |
| GB | 1312656 A | 4/1973 |

OTHER PUBLICATIONS

Product insert commercially available from Becton, Dickinson and Company for BD Microtainer Chemistry Tubes.
Product insert commercially available from Becton, Dickinson and Company for BD Capillary Collection, 2004.
Product insert commercially available from Becton, Dickinson and Company for BD Microtainer Plasma Separator Tube, 2000.
Product insert commercially available from Becton, Dickinson and Company for BD Microtainer Tubes with BD Microgard Closure, 2003.
Product insert commercially available from Becton, Dickinson and Company for BD Microtainer Tubes with Microgard Closure—Tube Guide and Order of Draw, 2003.
Product insert commercially available from Becton, Dickinson and Company for BD Microtainer Tubes—Tube Guide and Order of Draw, 2003.
Product insert commercially available from Terumo for Venosafe.
Product Literature commercially available from Greiner Bio One at www.gbo.com/documents/ V01_Tube_Guide_000502_e.pdf.

* cited by examiner

CONTAINER ASSEMBLY AND SYSTEM FOR DETECTION THEREOF

CROSS-REFERENCE TO RELATED APPLICATIONS

This application claims priority to U.S. Provisional Patent Application Ser. No. 61/296,437 entitled "Container Assembly and System for Detection Thereof", filed Jan. 19, 2010, and to U.S. Provisional Patent Application Ser. No. 61/415,631 entitled "Cap Having Features to Allow Recognition of Specimen Collection Systems for Automated Laboratory Processing", filed Nov. 19, 2010, the entire disclosures of each of which are hereby incorporated by reference.

BACKGROUND OF THE INVENTION

Field of the Invention

The present invention relates to a biological sample collection container and a system to aid in detection and identification of the type of closure and container to facilitate automated processing of the biological sample and collection container.

Description of Related Art

Biological samples, such as blood samples, are typically collected in sample containers, such as blood collection tubes, and transported to a laboratory for analysis.

In many processes for analyzing biological samples, particularly in batch and serial processes where several samples are involved, it is desirable to improve throughput by providing a greater degree of automated control over various stages of the sample handling, preparation, and analysis processes and by providing better management of sample-related data.

In one aspect, instrumentation for the handling, preparation, and analysis of samples has become more automated. For instance, where the analytical instrument requires the blood collection tubes to be open before they are sorted, pretreated, sampled, and tested, the instrument may have an automatic decapping processer to automatically decap blood collection tubes. Many automatic decapping processers rely on an optical vision inspection system using a color charged coupled device (CCD) to confirm the presence of a tube to be decapped.

Automating the decapping of blood collection tubes is further complicated by the variety of available blood collection tubes, which may vary in diameter, height, and especially the variety of available closures to cover the blood collection tubes. Some closures unscrew from threading on the top of the blood collection tubes. These include closures for blood collection tube-specific caps manufactured by Sarstedt® of Germany, Braun, also of Germany, Meditech, Inc. of Bel Air, Md. and Greiner® of Austria. Another type of closure is a rubber stopper inserted into a blood collection tube, such as a Vacutainer® blood collection tube, which is removed by a pulling motion. An additional type of closure has a stopper with an outer shield such as Hemogard™ caps used on Vacutainer® blood collection tubes from Becton, Dickinson and Company. The closures may also differ in their composition—they may be rubber, plastic, etc.

Conventional specimen collection containers used for the collection of biological samples typically include a closure or cap that is color coded to allow medical personnel and/or automated processing systems to visually discern the contents of the collection container. Color coded caps easily and quickly identify the contents of the specimen collection container and/or intended testing procedure of the container to medical personnel and automated processing systems without requiring that a printed label be read to determine the relevant information. For example, a specimen collection container having a red cap may indicate that the contents of the container are to be analyzed for serum-based tests, whereas a specimen collection container having a green cap may indicate that the contents are to be analyzed for plasma-based tests. In certain cases, the color coded caps may indicate that a biological sample has been mixed with certain additive or amount of additive in order to prepare the sample for a certain testing procedure.

As more testing procedures are developed and additional sample preparation additives are employed, the number of colors required for color coded caps has increased. However, by increasing the number of color variations that are used for the caps, it has become increasingly difficult to properly distinguish one color coded cap from another. For example, if a dark green cap is used to identify one testing procedure to be performed on the contents of the container, a medium green cap is used to identify another testing procedure to be performed on the contents of the container, and a light green cap is used to identify yet another testing procedure to be performed on the contents of the container, then the likelihood that one color coded cap may be confused for another color coded cap increases. This is particularly true for automated processes that may have difficulty in distinguishing specific hues within a given color family, i.e., distinguishing dark green from medium green. Inaccuracies in the process of determining cap color can result in the incorrect testing procedure being performed on the contents of a specific specimen collection container. In other instances, specimen collection containers may be inaccurately provided to a specific testing apparatus that is incompatible with the specimen collection container. In other instances, certain closure coloration can sometimes result in difficulty in automatic discrimination of closures by certain optical imaging systems and software—i.e., an optical vision inspection system fails to detect the presence of a closed blood collection tube and therefore fails to, for example, decap the blood collection tube and thereby reduce the throughput.

Furthermore, instrument and automation manufacturers have attempted to use the color of the closure for detection by an optical imaging system and software to automate the sorting of the blood collection tubes into similar types for further downstream analysis. This approach has inherent issues as even subtle color variation of the caps can prevent consistently accurate classification by the optical imaging system.

It would therefore be advantageous to provide an improved inspection system to detect closures without regard to coloration and with the added capability of allowing a more consistent and accurate identification of the type of tube for subsequent sorting and analytical processing.

It would also be advantageous to provide a system for providing a wide range of visual identifiers to easily identify the contents of a specimen collection container and/or the desired testing procedure to be performed on the contents of the specimen collection container. A need further exists to expand the current usage of color coded caps for quickly and easily identifying the contents of the specimen collection container.

SUMMARY OF THE INVENTION

The present invention is directed towards a biological sample collection container and a system to aid detection, and identification of the type of closure and container to facilitate automated processing of the biological sample and collection container. The present invention is also directed to a cap for a specimen collection container which enables an automated processing system to identify the contents of the specimen collection container. More specifically, an embodiment of the present invention relates to a cap for a specimen collection container which enables an automated processing system to identify the appropriate testing procedure to be performed on the contents of the specimen collection container based on visual indicators present on the cap.

In accordance with an embodiment of the present invention, a device for collecting a biological sample includes a collection container having a first end, a second end, and a sidewall extending therebetween. The device also includes at least one closure for sealing at least one of the first end and the second end, and one or more fluorescent compounds, wherein the one or more fluorescent compounds are disposed on the container.

In certain configurations, the one or more fluorescent compounds are molded into at least one of the container and the closure. The one or more fluorescent compounds may be disposed on at least one of an outer surface of the tube or an outer surface of the closure. Optionally, the closure may also include a stopper and a shield. In certain configurations, the one or more fluorescent compound may be molded into the shield. Alternatively, the one or more fluorescent compound may be molded into the stopper. The closure may also include a cap and a septum.

In accordance with an embodiment of the present invention, a device for collecting a biological sample includes a collection container having a first end, a second end, and a sidewall extending therebetween. The device also includes at least one closure for sealing at least one of the first end and the second end, and one or more fluorescent compounds, wherein the one or more fluorescent compounds are disposed within the container.

In certain configurations, the one or more fluorescent compounds are molded into at least one of the container and the closure. The one or more fluorescent compounds may be disposed on at least one of an outer surface of the tube or an outer surface of the closure. Optionally, the closure may also include a stopper and a shield. In certain configurations, the one or more fluorescent compound may be molded into the shield. Alternatively, the one or more fluorescent compound may be molded into the stopper. The closure may also include a cap and a septum.

In accordance with an embodiment of the present invention, a device for collecting a biological sample includes a collection container having a first end, a second end, and a sidewall extending therebetween. The device also includes at least one closure for sealing at least one of the first end and the second end, and one or more fluorescent compounds, wherein the one or more fluorescent compounds are disposed on the closure.

In certain configurations, the one or more fluorescent compounds are molded into at least one of the container and the closure. The one or more fluorescent compounds may be disposed on at least one of an outer surface of the tube or an outer surface of the closure. Optionally, the closure may also include a stopper and a shield. In certain configurations, the one or more fluorescent compound may be molded into the shield. Alternatively, the one or more fluorescent compound may be molded into the stopper. The closure may also include a cap and a septum.

In accordance with an embodiment of the present invention, a device for collecting a biological sample includes a collection container having a first end, a second end, and a sidewall extending therebetween. The device also includes at least one closure for sealing at least one of the first end and the second end, and one or more fluorescent compounds, wherein the one or more fluorescent compounds are disposed within the closure.

In certain configurations, the one or more fluorescent compounds are molded into at least one of the container and the closure. The one or more fluorescent compounds may be disposed on at least one of an outer surface of the tube or an outer surface of the closure. Optionally, the closure may also include a stopper and a shield. In certain configurations, the one or more fluorescent compound may be molded into the shield. Alternatively, the one or more fluorescent compound may be molded into the stopper. The closure may also include a cap and a septum.

In accordance with another embodiment of the present invention, a method for identifying a feature of a sample collection container includes providing a sample collection container adapted for joining with a closure, wherein the collection container contains one or more fluorescent compounds. The method also includes providing the sample collection container for communication with a fluorescence detection station including a fluorescence excitation light source and a detector, wherein the sample collection container is illuminated with fluorescence excitation light from said light source, and wherein the presence of a fluorescent signal from the one or more fluorescent compounds is detected by a detector to identify a feature of the sample collection container.

The feature may indicate a content of the sample collection container. Alternatively, the feature may indicate an intended testing procedure to be performed on a content of the sample collection container. In certain configurations, the sample collection container is a blood collection tube.

In accordance with another embodiment of the present invention, a method for identifying a feature of a sample collection container includes providing a sample collection container adapted for joining with a closure, wherein the closure contains one or more fluorescent compounds. The method also includes providing the closure for communication with a fluorescence detection station including a fluorescence excitation light source and a detector, wherein the closure is illuminated with fluorescence excitation light from said light source, and wherein the presence of a fluorescent signal from the one or more fluorescent compounds is detected by a detector to identify a feature of the closure and/or sample collection container.

The feature may indicate a content of the sample collection container. Alternatively, the feature may indicate an intended testing procedure to be performed on a content of the sample collection container. In certain configurations, the sample collection container is a blood collection tube.

In accordance with another embodiment of the present invention, a method for identifying a sample collection container includes providing a sample collection container adapted for joining with a closure, wherein the collection container comprises one or more fluorescent compounds having a characteristic fluorescent spectra. The method further includes providing the sample collection container in communication with a fluorescence detection station comprising a fluorescence excitation light source and a detector, wherein the sample collection container is illuminated with fluorescence excitation from the light source. The method also includes measuring the fluorescent spectra of the one or more fluorescent compounds, and identifying the sample collection container by comparing the measured fluorescent spectra with predetermined fluorescent spectra.

In certain configurations, the sample collection container is a blood collection tube. In certain other configurations, the measured fluorescent spectra is compared against a library of known fluorescent spectra to identify a feature of the sample collection container. Optionally, the feature may be a content of the sample collection container. Alternatively, the feature may be an intended testing procedure to be performed on a content of the sample collection container. In certain configurations, the measured fluorescent spectra may be compared against a library of known fluorescent spectra to discern the sample collection container from other collection containers.

In accordance with another embodiment of the present invention, a method for identifying a sample collection container includes providing a sample collection container adapted for joining with a closure, wherein the closure comprises one or more fluorescent compounds having a characteristic fluorescent spectra. The method further includes providing the closure in communication with a fluorescence detection station comprising a fluorescence excitation light source and a detector, wherein the closure is illuminated with fluorescence excitation from the light source. The method also includes measuring the fluorescent spectra of the one or more fluorescent compounds, and identifying the closure and/or the sample collection container by comparing the measured fluorescent spectra with predetermined fluorescent spectra.

In certain configurations, the sample collection container is a blood collection tube. In certain other configurations, the measured fluorescent spectra is compared against a library of known fluorescent spectra to identify a feature of the sample collection container. Optionally, the feature may be a content of the sample collection container. Alternatively, the feature may be an intended testing procedure to be performed on a content of the sample collection container. In certain configurations, the measured fluorescent spectra may be compared against a library of known fluorescent spectra to discern the sample collection container from other collection containers.

In accordance with another embodiment of the present invention, a closure includes a top surface and an annular skirt depending therefrom. The annular skirt includes a first portion having a first visual identifier and a second portion having a second visual identifier, the second visual identifier being different from the first visual identifier.

In certain configurations, the first visual identifier is a first color, and the second visual identifier is a second color, the second color being different from the first color. Optionally, either the first visual identifier or the second visual identifier includes one or more fluorescent compounds having a characteristic fluorescent spectra. The first visual identifier may include a first fluorescent compound having a characteristic fluorescent spectra and the second visual identifier may include a second fluorescent compound having a characteristic fluorescent spectra, the second fluorescent compound being different from the first fluorescent compound.

The closure may further include a stopper at least partially disposed within the annular skirt, wherein at least one of the annular skirt and the stopper are configured for closing a container. The top surface and the first portion of the annular skirt may have the same visual identifier. In certain configurations, the second portion of the closure may be printed over at least a portion of the first portion. The first portion may be the base material of the closure.

In certain configurations, the first portion and the second portion are co-formed. In other configurations, the first portion and the second portion are formed of the same material. Optionally, the first portion and the second portion are formed of different materials. In one embodiment, the first portion may be adjacent the top surface and the second portion is adjacent a bottom surface of the annular skirt. In another embodiment, the first portion includes a first region adjacent the top surface and a second region adjacent a bottom surface of the annular skirt, and the second portion is disposed between the first region of the first portion and the second region of the first portion. In yet another embodiment, the first portion includes a first region adjacent a first depending sidewall and a second region adjacent a second depending sidewall, and the second portion is disposed between the first region of the first portion and the second region of the first portion. In another embodiment, the second portion is disposed between a first region of the second portion and a second region of the first portion. In another embodiment, the first portion and the second portion form a repeating pattern. In yet another embodiment, at least a portion of the second portion is fully surrounded by the first portion.

Optionally, the top surface of the closure may include a pierceable portion. In certain configurations, the pierceable portion is resealable.

In accordance with another embodiment of the present invention, a container assembly includes a collection container having a closed bottom, an open top portion, and a sidewall extending therebetween adapted to receive a specimen sample therein. The container assembly also includes a closure having a top surface and an annular skirt depending therefrom, wherein the annular skirt includes a first portion having a first visual identifier and a second portion having a second visual identifier, the second visual identifier being different from the first visual identifier.

The first visual identifier may be a first color and the second visual identifier may be a second color, the second color being different from the first color. In certain configurations, either the first visual identifier or the second visual identifier includes one or more fluorescent compounds having a characteristic fluorescent spectra. The first visual identifier may include a first fluorescent compound having a characteristic fluorescent spectra, and the second visual identifier may include a second fluorescent compound having a characteristic fluorescent spectra, the second fluorescent compound being different from the first fluorescent compound.

The first portion and the second portion may provide visual identification of a content of the collection container. The first portion and second portion may provide visual identification of an intended testing procedure to be performed on a content of the collection container. The closure may be adapted for visual recognition by an automated processing system.

In accordance with yet another embodiment of the present invention, an automated processing system includes a directing system for directing the location of collection containers. The collection containers each include a closed bottom, an open top portion, and a sidewall extending therebetween, adapted to receive a specimen sample therein. The collection containers also include a closure having a top surface and an annular skirt depending therefrom, wherein the annular skirt includes a first portion having a first visual identifier and a second portion having a second visual identifier, the second visual identifier being different from the first visual identifier. The automated processing system further includes an automated visual identifier system for selectively identifying the collection containers to be directed by the directing system by the first portion and the second portion of the annular skirt of the closure.

The various features, objects, and advantages of the invention will become apparent to those skilled in the art in view of the following detailed description and the annexed drawings which disclose preferred embodiments of the invention.

DESCRIPTION OF PREFERRED EMBODIMENTS

For purposes of the description hereinafter, spatial orientation terms, if used, shall relate to the referenced embodiment, as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 13:
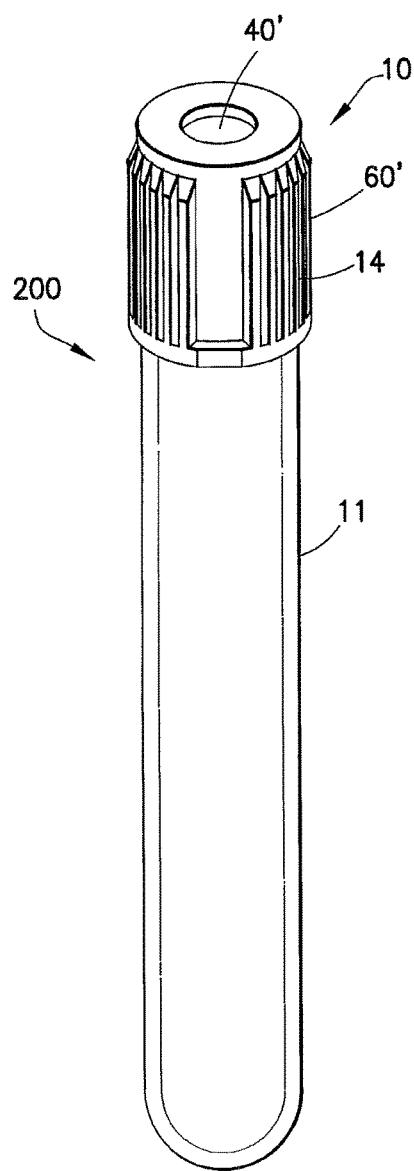
FIG. 13 is a perspective view of a conventional 13 millimeter sample collection container and closure assembly for use in accordance with an embodiment of the present invention.
Figure 15:
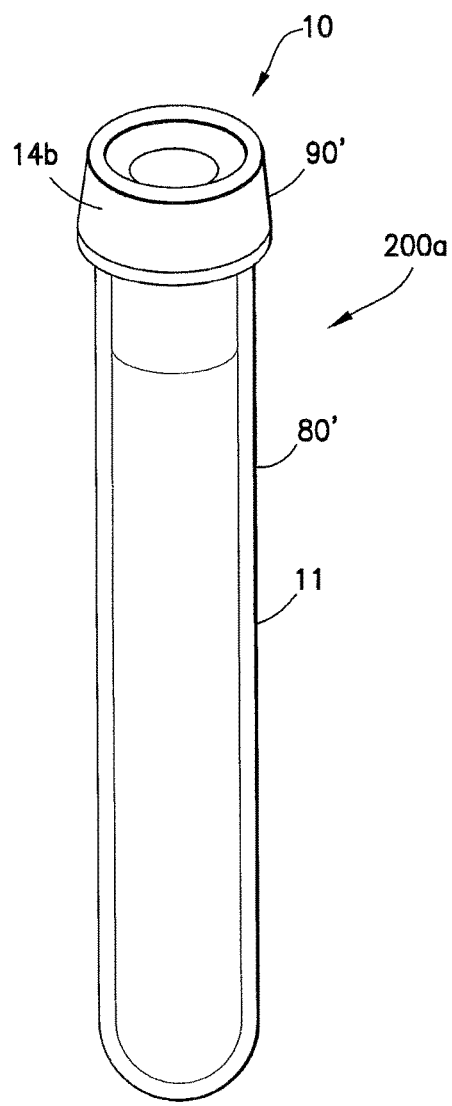
FIG. 15 is a perspective view of a 16 millimeter sample collection container and closure assembly for use in accordance with an embodiment of the present invention.
Figure 14:
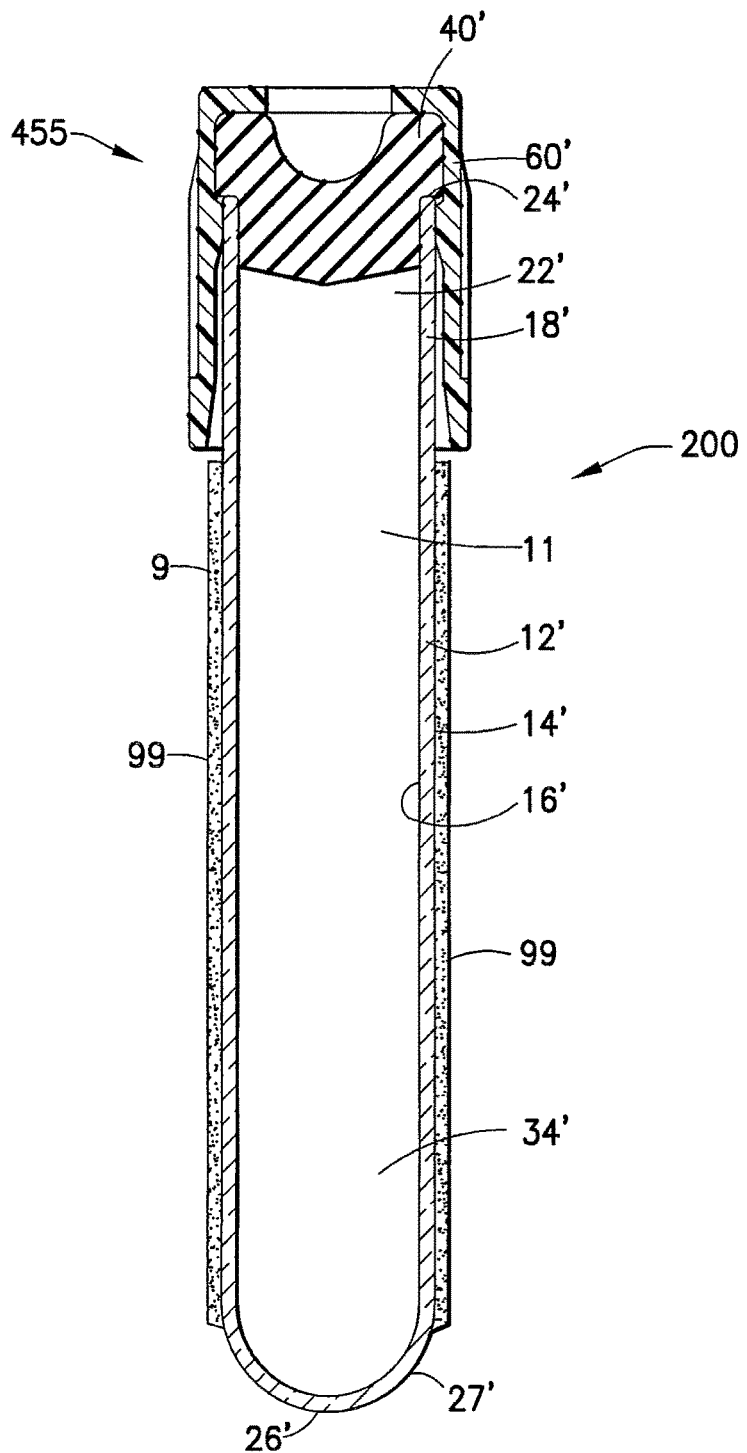
FIG. 14 is a cross sectional side view of the container and closure of FIG. 13 in accordance with an embodiment of the present invention.

Referring to FIGS. 1-5, the present invention is directed to a cap or closure 10 having a top surface 12 and an annular skirt 14 depending therefrom in which the annular skirt 14 includes a first portion 30 having a first visual identifier, and a second portion 32 having a second visual identifier, as shown in FIGS. 16-57, with the second visual identifier being different from the first visual identifier. Referring to FIGS. 13-15, the present invention is also directed to a collection assembly 200, 200a having a sample collection container 11 and a closure 10, wherein at least one of the sample collection container 11 and the closure 10 include a visual identifier, such as a fluorescent compound, as will be discussed herein.

Referring to FIGS. 1-5, the closure 10 of the present invention is intended for closing the open end of a specimen collection container, such as those described in U.S. Pat. Nos. 6,910,597, 6,749,078, and 6,612,997, the entire disclosures of each of which are hereby incorporated by reference, is shown. The closure 10 may be used in connection with collection containers used for the collection, storage, and eventual transfer of biological specimens, including blood samples, for purposes of diagnostic testing. The closure 10 may be disposed on the specimen collection container so as to cover and seal the specimen collection container and any sample contained therein. The specimen collection container may be a biological specimen collection container for proteomics, molecular diagnostics, chemistry sampling, blood, or other bodily fluid collection, coagulation sampling, hematology sampling, and the like, and may be either evacuated or non-evacuated. In one embodiment, the specimen collection container can be particularly suited for receipt and storage of a bodily fluid specimen. In a further embodiment, the specimen collection container is particularly suited for receipt and storage of blood, such as venous blood or capillary blood, from an animal or human patient.

With reference to FIGS. 1-5, a closure 10 is provided for covering the top opening of a specimen collection container and sealing the internal cavity defined therein, as is conventionally known. The cap 10 includes a top portion 12 and an annular skirt portion 14 depending from the top portion 12. The annular skirt portion 14 includes an exterior surface 16 and an interior surface 18. Gripping features 20, such as raised ridges or knurled features, may be provided on the exterior surface 16 to assist in placement and removal of the closure 10 on the specimen collection container. Gripping features 20 may extend along a portion of the annular skirt portion 14, or may extend the entire length of the annular skirt portion 14 extending between the top portion 12 and a bottom portion 22.

The top portion 12 may define a solid substantially flat surface, or may define a substantially flat rigid portion 24 surrounding a pierceable portion 26. In certain configurations, the pierceable portion 26 may be penetrated by a needle cannula and/or a diagnostic or sampling probe. In still further configurations, the pierceable portion 26 may be self-resealing. Optionally, the rigid portion 24 may include indicia or other indicating symbology. It is further intended herein that the closure 10 of the present invention may include a stopper (not shown) as disclosed in U.S. Pat. No. 6,562,300, incorporated herein by reference, as is conventionally known. It is further intended herein that at least one of the annular skirt 14 and the stopper may be configured for closing the open end of a specimen collection container.

With reference to FIGS. 6-10, a similar closure 10A of the present invention includes a top portion 12A and an annular skirt portion 14A depending from the top portion 12A. The annular skirt 14A may similarly include gripping features 20A and a bottom portion 22A. Likewise, the top portion 12A may also include a substantially flat portion 24A and a pierceable portion 26A. It is also to be appreciated that many other structural cap configurations may be employed with the present invention.

Figure 1:
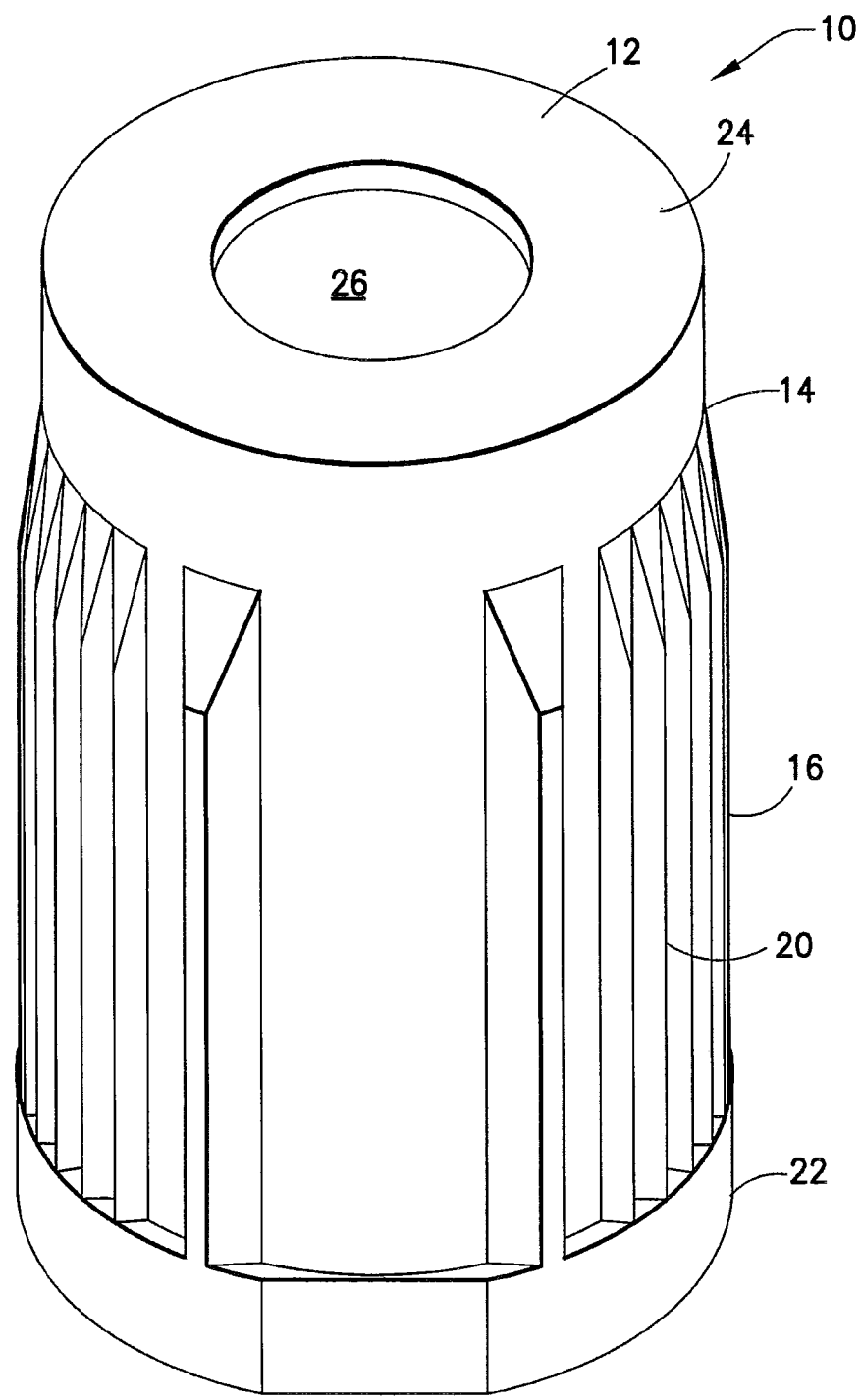
FIG. 1 is a perspective view of a closure for closing a specimen collection container in accordance with an embodiment of the present invention.
Figure 2:
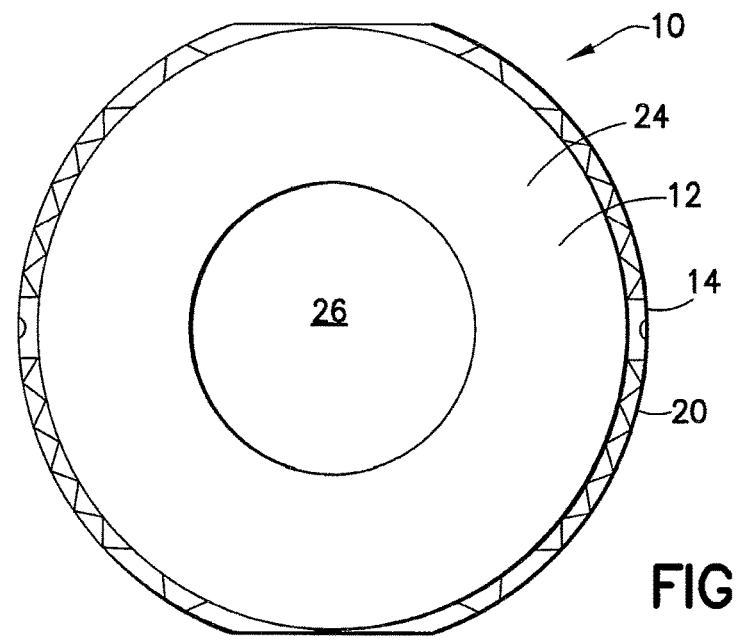
FIG. 2 is a top view of the closure of FIG. 1 in accordance with an embodiment of the present invention.
Figure 3:
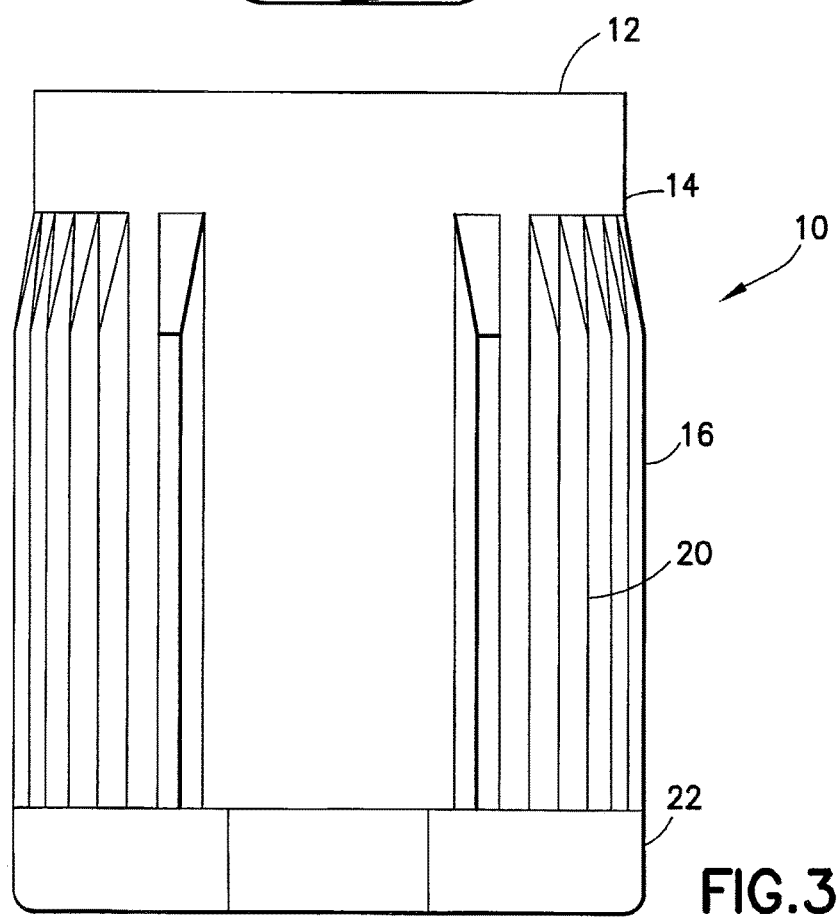
FIG. 3 is a front view of the closure of FIG. 1, with the rear view being a mirror image thereof, in accordance with an embodiment of the present invention.
Figure 4:
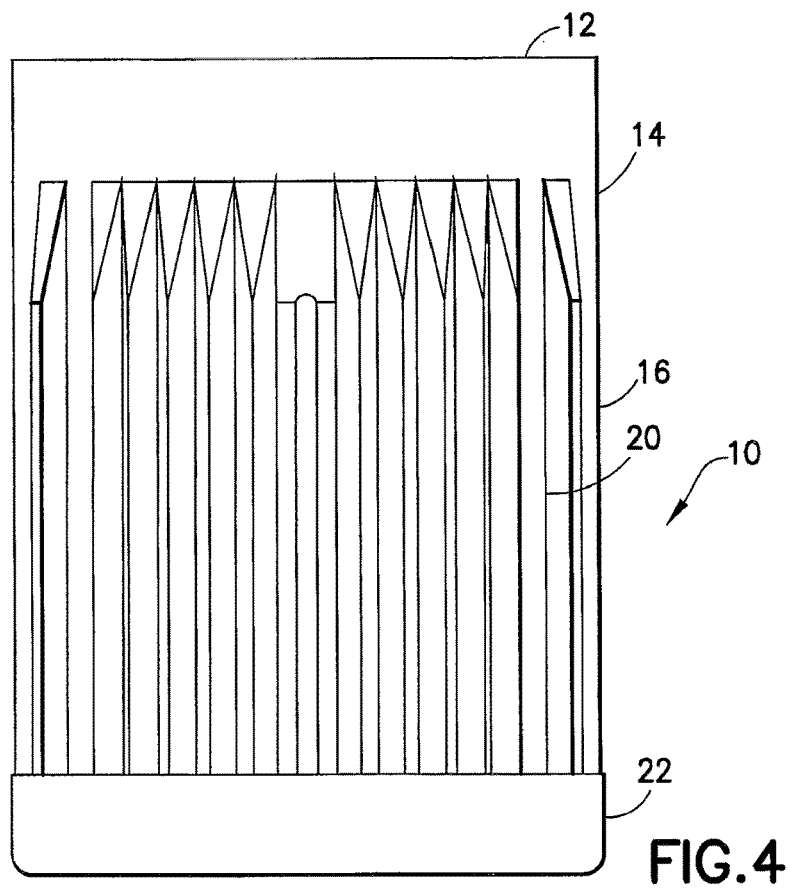
FIG. 4 is a left side view of the closure of FIG. 1, with the right side view being a mirror image thereof, in accordance with an embodiment of the present invention.
Figure 5:
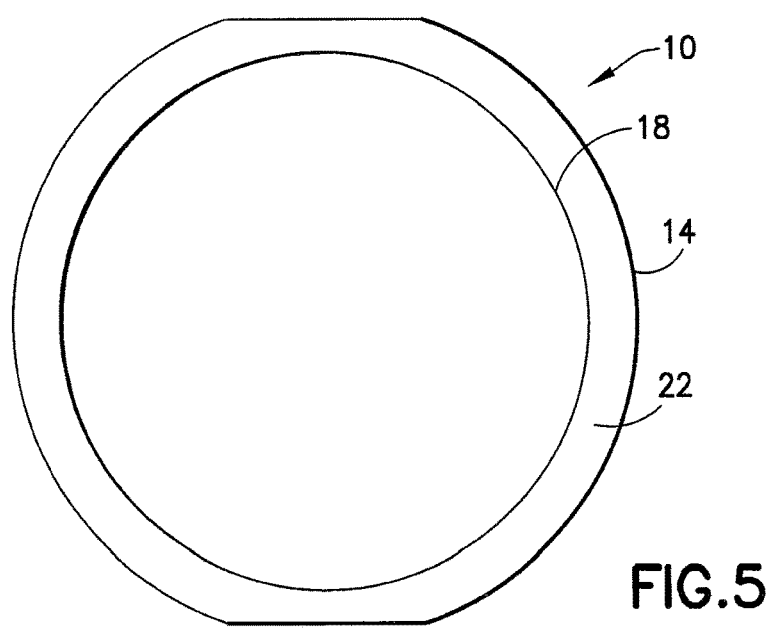
FIG. 5 is a bottom view of the closure of FIG. 1 in accordance with an embodiment of the present invention.
Figure 6:
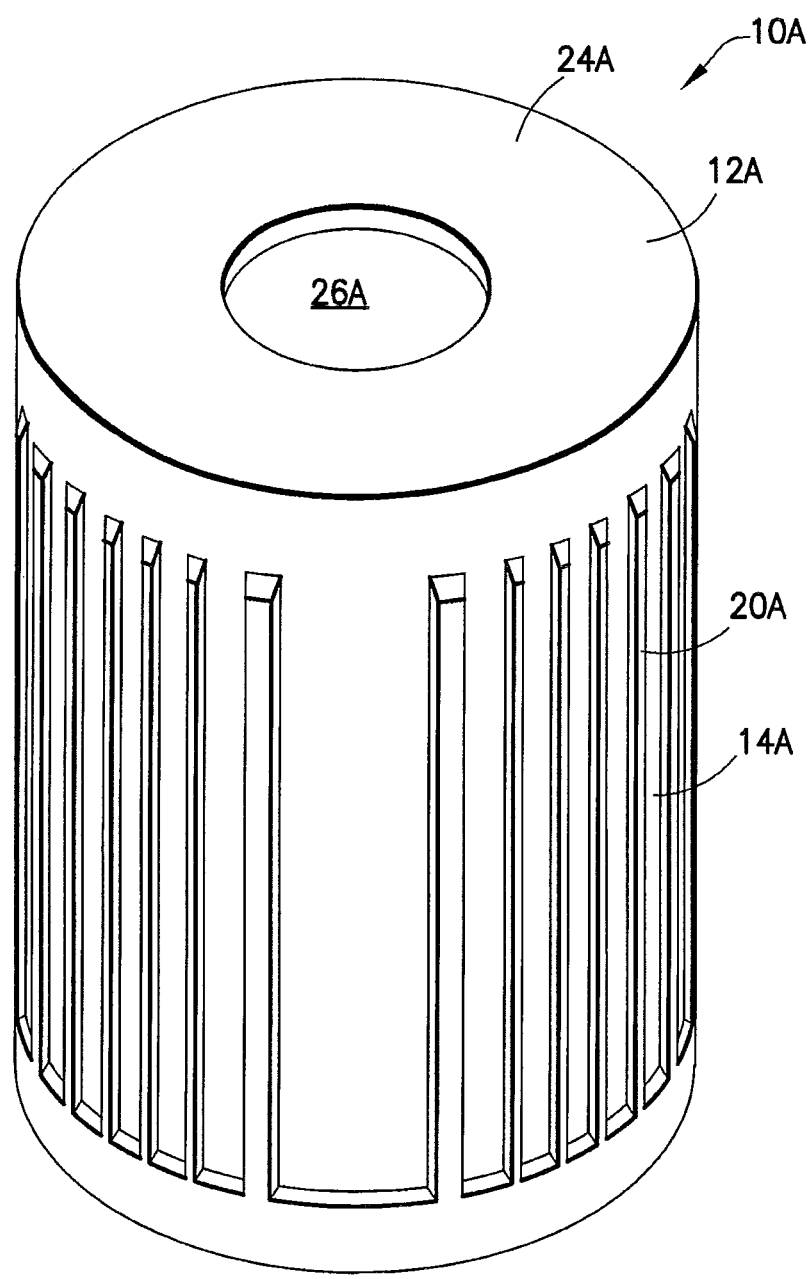
FIG. 6 is a perspective view of a closure for closing a specimen collection container in accordance with an embodiment of the present invention.
Figure 7:
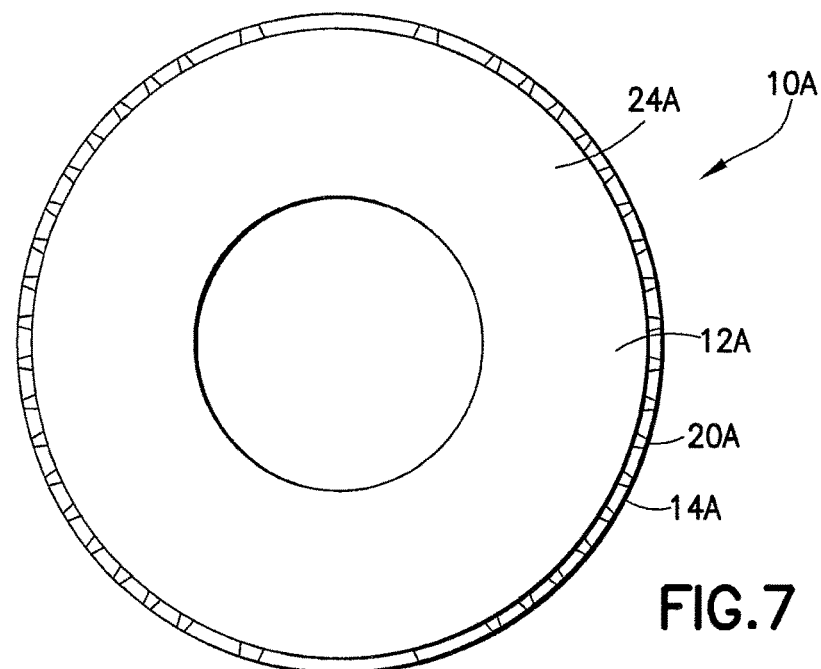
FIG. 7 is a top view of the closure of FIG. 6 in accordance with an embodiment of the present invention.
Figure 8:
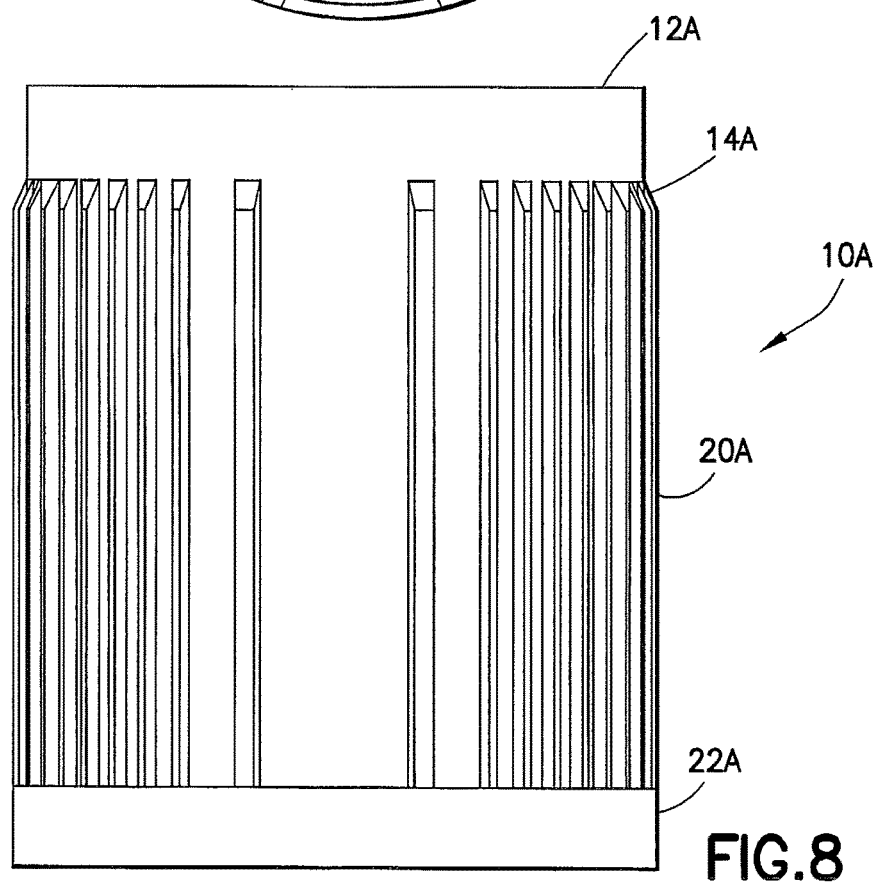
FIG. 8 is a front view of the closure of FIG. 6, with the rear view being a mirror image thereof, in accordance with an embodiment of the present invention.
Figure 9:
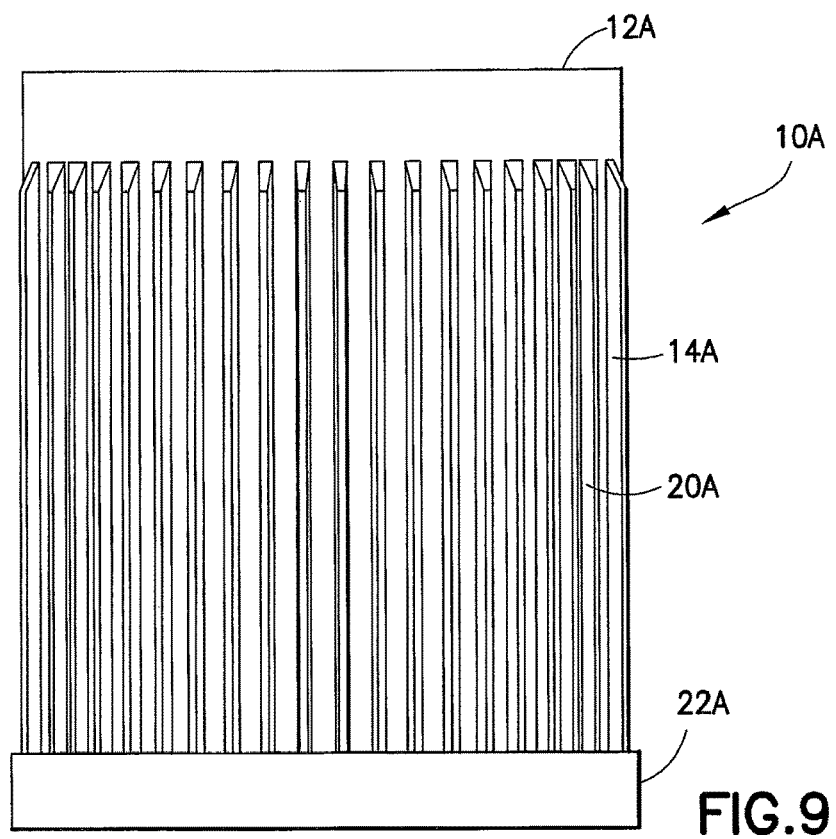
FIG. 9 is a left side view of the closure of FIG. 6, with the right side view being a mirror image thereof, in accordance with an embodiment of the present invention.
Figure 10:
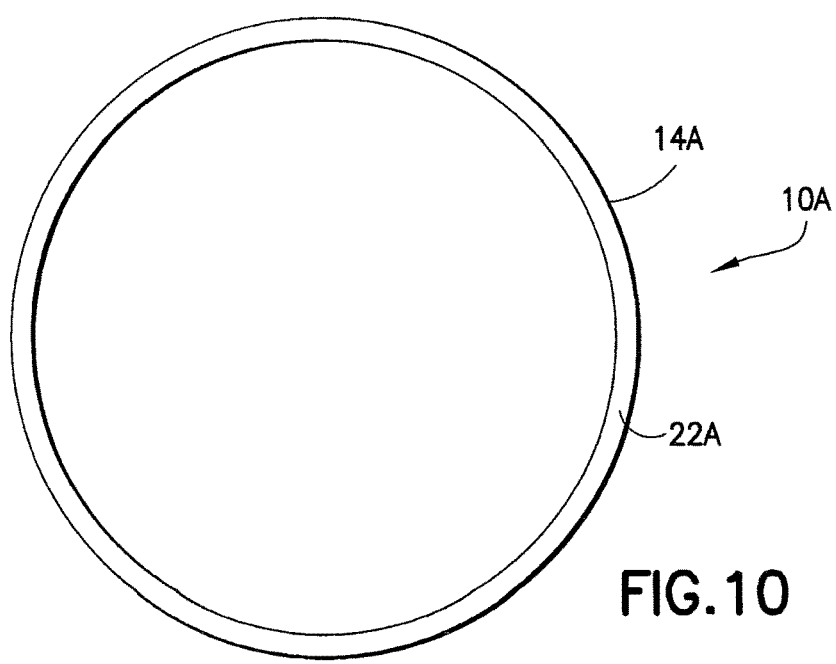
FIG. 10 is a bottom view of the closure of FIG. 6 in accordance with an embodiment of the present invention.
Figure 11:
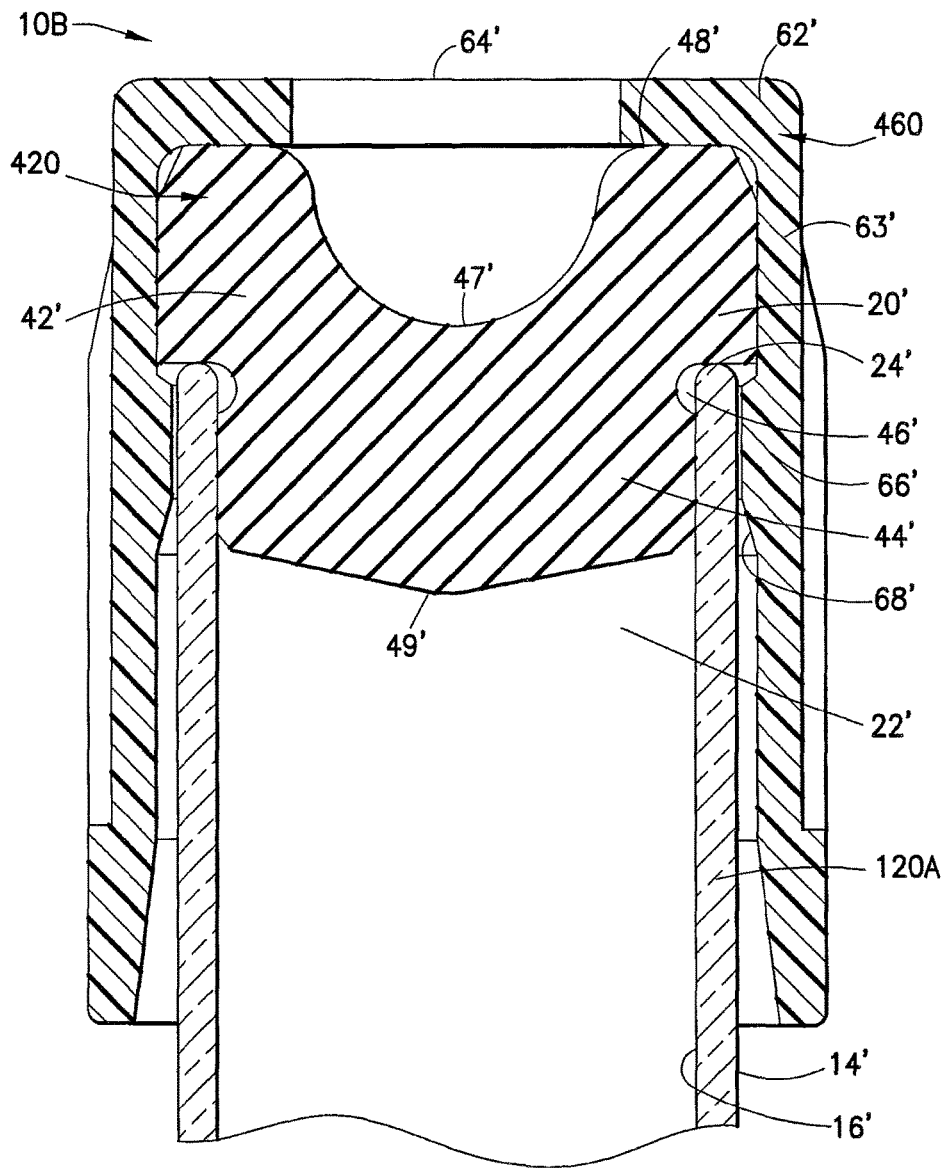
FIG. 11 is a cross-sectional side view of a container and closure in accordance with an embodiment of the present invention.

With reference to FIG. 11, another suitable closure 10B of the present invention includes a stopper 420 and a shield 460. Stopper 420 includes a flange portion 42' and a sealing portion 44', having a reduced diameter as compared to the upper flange portion 42', which forms an interference fit seal with inner surface 16' of sample collection container 120A. A radial notch 46' may be defined within the stopper 420 between the upper portion 42' and lower portion 44' to assist in the sealing of the stopper 420 with the inner surface 16' of the sample collection container 120A. Optionally, a finger well 47' may be positioned centrally in the top surface 48' of stopper 420, and the bottom surface 49' of stopper 420 may be generally convex. In certain embodiments, the stopper of the closure may be formed of a pierceable material such as an elastomer (for example bromo butyl rubber or a thermoplastic elastomer).

Referring again to FIG. 11, extending over the top of stopper 420 is a plastic cap or shield 460 which is co-molded from a flexible thermoplastic resin and a fluorescent compound and which includes a top surface 62' for extending over the top surface 48' of stopper 420. The shield 460 may include an annular skirt 63' depending from top surface 62'. The top surface 62' may define an opening 64' through which a needle cannula or probe may pass for insertion and penetration through the stopper 420. The shield 460 may include an integral annular abutment 66' for engaging an outer surface 14' of the specimen collection container 120A and for restraining a portion of the stopper 420 within the interior of the shield 460.

Figure 12:
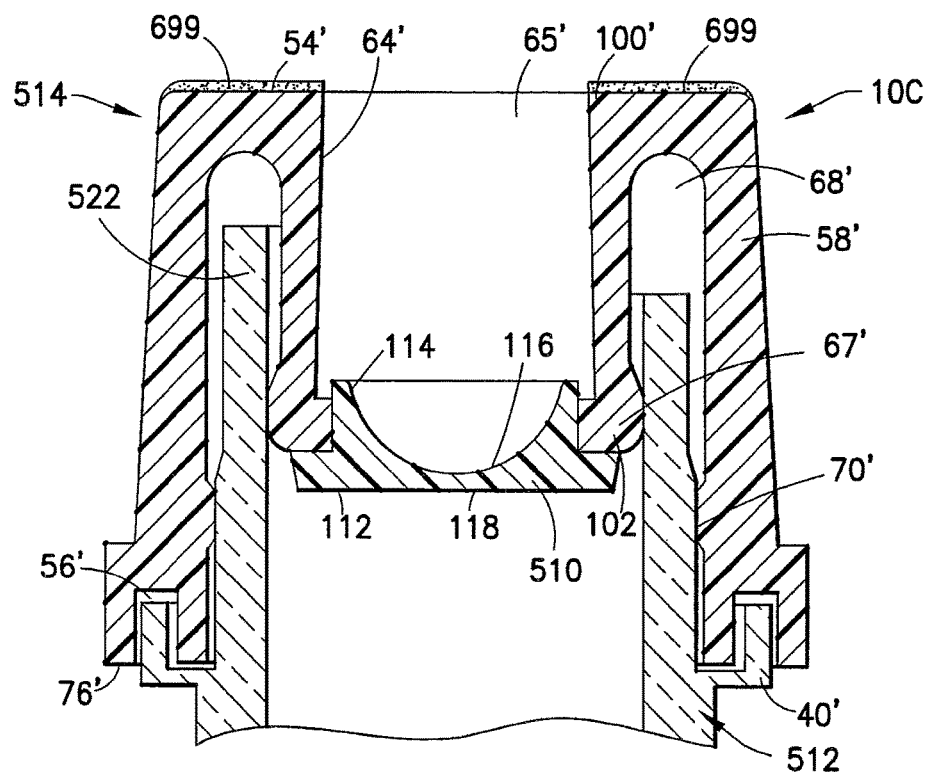
FIG. 12 is a cross-sectional side view of a container and closure in accordance with an embodiment of the present invention.

With reference to FIG. 12, another suitable closure 10C, similar to the closure as disclosed in U.S. Pat. No. 6,426,049 to Rosen et al., which is hereby incorporated by reference in its entirety, of the present invention includes a cap body 514 and a septum 510. Closure 10C seals the open top 522 of container 512 via a sealing ring 67' positioned on inverted recessed skirt portion 64' which provides a seal against the inner surface of the container 512 side wall. The inverted recessed skirt portion of cap 514 includes an open upper extent 100', an opposed open lower extent 102, and a central passageway 65' therebetween which provides access through the cap and into the container. Cap body 514 supports a septum 510 at lower extent 102 of recessed skirt portion 64'.

Referring again to FIG. 12, septum 510 may have a disc-like molded membrane suitable for penetration by a needle cannula or a probe. Septum 510 may include a planar portion 112 and an upwardly extending annular ridge 114 for guiding the needle cannula or probe (not shown) to a centrally located portion 118 for penetration. Annular ridge 114 may have a diameter which allows it to be force-fitted within open lower extent 102 of recessed skirt portion 64'. Planar portion 112 may face towards the interior of the container 512, as shown, and annular ridge 114 may define a concave surface 116 in opposition to planar portion 112 to facilitate easy penetration by a cannula or probe used to extract a sample from the interior of the container. In one embodiment, the portion 118 may be penetrated by a force of about 2 pounds.

FIGS. 13-15 illustrate sample collection containers, such as blood collection tubes 11, suitable for use with the closures 10, 10A, 10B, and 10C as described herein in accordance with an embodiment of the present invention.

FIGS. 13-14 illustrate a blood collection tube 11 with a closure 10 having a stopper 40' and a shield 60' having an annular skirt portion 14. FIG. 15 illustrates a blood collection tube 80' with a closure 10 having a stopper 90' and an annular skirt portion 14b as disclosed in U.S. Pat. No. 6,602,206 to Niermann et al., which is hereby incorporated by reference in its entirety.

As shown in FIG. 14, sample collection container 11 includes a sidewall 12' having an outer surface 14' and an inner surface 16' and extending between an upper portion 18' to a lower portion 27'. Upper portion 18' includes an open end 22' and may include a rim 24'. Lower portion 27' includes a closed bottom end 26'. The sidewall 12' defines an interior volume 34' defined between rim 24' and closed bottom end 26'.

Some suitable materials used to manufacture sample collection containers, such as the blood collection tubes and closures as shown herein include polypropylene, polyethylene, polyethyleneterephthalate, polystyrene, polycarbonate, cellulosics, polytetrafluoroethylene, and other fluorinated polymers, polyolefins, polyamides, polyesters, silicones, polyurethanes, epoxies, acrylics, polyacrylates, polysulfones, polymethacrylates, polyetheretherketone (PEEK), polyimide, and fluoropolymers such as poytetrafluoroethylene (PTFE), fluorinated ethylene propylene (FEP), ethylene tetrafluoroethylene, poly(vinylidene fluoride), polyvinylidene difluoride (PVDF), and perfluoroalkoxy resins. Glass products including silica glass may also be used to manufacture suitable sample collection containers. One exemplary glass product is PYREX® (available from Corning Glass, Corning, N.Y.).

The sample collection container 11 may include a predetermined amount of additive dependent on the volume of specimen to be introduced into the sample collection container 11 and/or the intended testing procedure to be performed on the contents of the sample collection container 11. For example, a plasma preparation tube will contain an anticoagulant additive, whereas a serum preparation tube will contain a pro-coagulant additive.

Typically, specimen collection containers 11 are generally processed to provide various additives within the specimen collection container 11. For example, additives useful in blood or urine analysis, e.g., procoagulants or anticoagulants, are often provided within a specimen collection container 11 prior to collection or analysis of a blood or urine specimen. As known in the art, blood analysis is often performed on serum, and procoagulants are typically used to enhance the rate of clotting. Such procoagulants may include silica particles or enzyme clot activators such as elagic acid, fibrinogen, and thrombin. If plasma is desired for analysis, an anticoagulant is generally used to inhibit coagulation, such that blood cells can be separated by centrifugation. Such anticoagulants include chelators such as oxalates, citrate, and EDTA, and enzyme inhibitors such as heparin. Additives are disposed in the primary containers in any suitable manner, liquid or solid, including dissolution in a solvent, or disposing in powdered, crystallized, or lyophilized form.

Additional additives can include a stabilizing agent for stabilizing or inhibiting the degradation of a component within the biological sample such as nucleic acid or proteins in a blood sample. Examples of suitable agents for stabilizing and preserving nucleic acids and/or preventing gene induction include cationic compounds, detergents, chaotropic substances, and mixtures thereof, which are described in U.S. Pat. No. 6,821,789. A protein stabilizing agent may include at least one protease inhibitor. Suitable examples include, but are not limited to, inhibitors of proteases such as serine proteases, cysteine proteases, aspartic proteases, metalloproteases, thiol proteases, exopeptidases, and the like, which are described in U.S. Pat. No. 7,309,468.

The blood collection tube may also contain carrier media (e.g., water or alcohol), stabilizing media (e.g., polyvinylpyrrolidone, trehalose mannitol, etc.), and/or one or more other additives for treating the biological sample. Suitable additives include, but are not limited to, phenol, phenol/chloroform mixtures, alcohols, aldehydes, ketones, organic acids, salts of organic acids, alkali metal salts of halides, fluorescent dyes, antibodies, binding agents, and any other reagent or combination of reagents normally used to treat biological samples for analysis. Other potential additives include antioxidants and reducing agents, which may help preserve protein confirmation, e.g., preserve sulfhydryl group couplings. It may also be advantageous to include a buffering agent.

It is also possible to include separators in the blood collection tube, e.g., density gradient separators in mechanical or non-mechanical form (e.g., thixotropic gels). Such separators provide for cell separation or plasma separation, for example. See, e.g., European Patent applications EP1006360, EP1006359, EP1005909, EP1014088, EP1106253, and EP0384331, and U.S. Pat. Nos. 4,140,631, 4,770,779, 4,946,601, 6,406,671, 6,280,400, and 6,225,123.

The blood collection tube and closure of the various embodiments of the invention are capable of being formed in any desired size. For example, a tube according to one embodiment is capable of being formed as a conventional evacuated tube 50-150 mm in length and 10-20 mm internal diameter. In particular, standard evacuated tubes, which are 75 or 100 mm in length and have a 13 or 16 mm external diameter, or standard microcollection tubes, which are 40-45 mm long and have a 5-10 mm internal diameter, are possible. Typical wall thicknesses of conventional blood collection tubes, e.g., about 25 to about 50 ml, more typically about 30 to about 40 ml, are possible in tubes according to the invention.

Preparation of a blood collection tube for use in specimen collection, after molding, may include placement of a density gradient separator, disposing an additive, subjecting the container to an evacuated chamber with a pressure below atmospheric pressure, applying a seal such as an elastomeric stopper or pierceable membrane, and sterilizing the container by a process such as irradiation (e.g., with cobalt 60 radiation), ethylene oxide gas exposure, or electron-beam exposure. (Note that several of these steps may be performed in an order other than that presented above).

In accordance with an aspect of the present invention, at least one of the closure 10, 10A, 10B, and 10C and the sample collection container 11 include at least one visual identifier for identifying a feature of the sample collection assembly 200. Specifically, at least one of the closure 10, 10A, 10B, and 10C and the sample collection container 11 may include at least one fluorescent compound for providing a visual identification of the contents of the sample collection container and/or the intended testing procedure to be performed on the contents of the sample collection container.

As used herein, the term "fluorescent compound" means any compound or molecule which provides luminescence that is caused by the absorption of radiation at one wavelength followed by nearly immediate radiation at a different wavelength. The subsequent radiation of the fluorescent compound may cease almost at once when the incident radiation stops, or may continue for a noticeable time after the initial incident radiation ceases, providing a phosphorescent effect.

In accordance with an embodiment of the present invention, fluorescent compounds may be co-molded with the closure 10 and/or the sample collection container 11 as part of the molding process. In another embodiment, the fluorescent compound may be co-molded with the stopper 40', as shown in FIG. 14, or septum 510, as shown in FIG. 12. In another embodiment, the fluorescent compound may be provided as a surface coating by spray coating or printing onto the component parts prior to assembly or onto finished products. Alternatively, a label impregnated with a fluorescent compound or printed with an ink containing a fluorescent compound may be applied to the closure or tube.

Fluorescent compounds suitable for use in connection with the present application may produce a bright fluorescence so that the fluorescence reaches detectable levels even when small amounts of the fluorophore(s) are present. Fluorescent compounds suitable for use in connection with the present application may also appear as invisible in the visible light spectrum to users under typical lighting conditions, but appear as detectable colorations under appropriate excitation. Fluorescent compounds suitable for use in connection with the present application also may be stable to irradiation-based sterilization. It is contemplated herein, that the fluorescent compound may be applied to the closure 10 and/or the sample collection container 11 either before or after a sterilization process is performed. It is also contemplated herein that the fluorescent compounds may be applied by spraying, dipping, rolling, misting and the like It is further contemplated herein that a substantial amount of the fluorescent compound may be wiped from the surface of the closure 10 and/or the container 11 after application, still leaving behind a sufficient quantity of fluorescent compound to provide a suitable fluorescent spectra under excitation.

Typically, when the fluorescent compound is excited the compound emits an image that is visually distinct from any autofluorescence that might be associated with the sample collection container either intrinsic to the plastics of the closure and/or tube or possibly unique to certain chromophores contained within the blood sample or tube additives. In certain embodiments, a fluorescent compound of the present invention has a long Stokes shift, i.e., the wavelength spectrum of excitation light should be greatly separated from the emission spectrum, such that selection of individual fixed wavelengths for excitation and emission will give an unambiguous signal only from actual fluorescence, and reduced or no detection of the excitation light at the selected emission wavelength.

In another embodiment, the fluorescent compound exhibits a high quantum yield, which further assists in the unambiguous detection of fluorescence. All of these attributes help to improve signal/noise during imaging, and reduce the power of the "black light" illumination required. In one embodiment, a fluorescent compound of the present invention will have an excitation that closely matches wavelength of commercial "black light" sources.

Suitable examples of fluorescent compounds include fluorescent dyes based on xanthene (such as fluorescein and rhodamine), aridines, anthraquinones, coumarins, diphenylmethanes, diphenylnapththymethanes, quinolines, stilbenes, and triphenylmethane which may be dissolved in a suitable solvent and sprayed onto or incorporated into an ink formulation and printed onto the stopper, shield, or tube. Alternatively, an ultraviolet fluorescent tracer, such as TR-1556 or TR-1566 Chromatint Fluorescent Tracer sold by Chromatech, Inc. or UVITEX OB commercialized by CIBA, may be molded with the appropriate polymer which forms the closure 10, 10A, 10B, 10C or the sample collection container 11.

The fluorescent compound may also include an infrared active dye including organic or inorganic or hybrid organic-inorganic compounds. In one embodiment, the infrared dye may have a strong absorption at a narrow wavelength, and may have strong absorption in the near infrared (NIR) region of the electromagnetic spectrum, i.e., in the region of 700 nm to 1200 nm. Examples of such NIR dyes are disclosed in JOEM Handbook 2 Absorption Spectra of Dyes for Diode Lasers, Matsuoka, Ky., bunshin Shuppan, 1990 and Chapter 2, 2.3 of Development and Market Trend of Functional Coloring Materials in 1990's, CMC Editorial Department, CMC, 1990, such as polymethine type coloring material, a phthalocyanine type coloring material, a dithiol metallic complex salt type coloring material, an anthraquinone type coloring material, a triphenylmethane type coloring material, an azo type dispersion dye, and an intermolecular CT coloring material. The representative examples include N-[4-[5-(4-dimethylamino-2-methylphenyl)-2,4-pentadienylidene]-3-methyl-2-,5-cyclohexadiene-1-ylidene]-N,N-dimethylammonium acetate, N-[4-[5-(4-dimethylaminophenyl)-3-phenyl-2-pentene-1-ylidene]-2,5-cyc-lohexadiene-1-ylidene]-N,N-dimethylammonium perchlorate, bis(dichlorobenzene-1,2-dithiol)nickel(2:1)tetrabutyl-ammonium, and polyvinylcarbazol-2,3-dicyano-5-nitro-1,4-naphthoquinone complex. Some specific commercial products that may be employed include Pro-jet 830NP, a modified copper phthalocyanine from Avecia of Blackley, Lancashire in the United Kingdom, and ADS 830A, an infra-red absorbing dye from American Dye Source, Inc. of Montreal, Quebec, Canada. Other examples of NIR dyes include 2,4,5,7-tetranitrofluorenone or (2,4,7-trinitrofluorenylidene)-malononitrile, which are described in U.S. Pat. No. 7,323,889, which is incorporated herein by reference in its entirety.

In another embodiment, a water soluble NIR dye may be utilized in accordance with an embodiment of the present invention. Examples of suitable water soluble NIR dyes include commercial products that include SDA 1910 (Abs. Max. 910 nm), SDA 6122 (Abs. Max. 868 nm), SDA 1868 (Abs. Max. 868 nm), SDA 8700 (Abs. Max. 844 nm), SDA 8208 (Abs. Max. 824 nm), SDB 4927 (Abs. Max. 822 nm), SDA 9362 (Abs. Max. 820 nm) SDA 7563 (Abs. Max. 819 nm), SDA 9158 (Abs. Max. 808 nm), SDA 1842 (Abs. Max. 807 nm), SDB 8662 (Abs. Max. 784 nm), SDA 1372 (Abs. Max. 782 nm), and SDD5712 (Abs. Max. 781 nm) from HW Sands Corp., SDA 8700 and SDB 4927.

In accordance with one embodiment, as shown in FIG. 14, a coating 99 containing a fluorescent compound has been applied to the outer surface 14' of sidewall 12'. In accordance with another embodiment, as shown in FIG. 12, a coating 699 containing a fluorescent compound has been applied to a portion of the closure 10C. Alternatively, the stopper 40', as shown in FIG. 14 may be co-molded with a fluorescent compound, or a coating containing a fluorescent compound applied to the outer surface of the shield 60'. Referring to FIG. 12, the septum 510 may be formed by co-molding a thermoplastic elastomer and a fluorescent compound.

With reference to FIGS. 1-10, it is contemplated herein that the annular skirt 14, 14A of the closure 10 may include a first portion 30 having a first visual identifier and a second portion 32 having a second visual identifier that is different from the first identifier, as shown in FIGS. 16-57. In one embodiment, one of the first and second visual identifiers is a fluorescent compound. In another embodiment, one of the first and second visual identifiers is a first fluorescent compound and the other of the first and second visual identifiers is a second fluorescent compound that is different than the first fluorescent compound. In yet another embodiment, one of the first and second visual identifiers is a fluorescent compound and the other of the first and second visual identifiers is a non-fluorescent material or region.

Alternatively, with reference to FIGS. 1-10, the annular skirt 14, 14A of the closure 10, 10A of the present invention includes a first portion 30 having a first color, and a second portion 32 having a second color, with the first color being different from the second color, as shown in FIGS. 16-57. As used herein, the phrase "the first color being different from the second color" means that the first color is visually discernable from the second color by either computerized scanning techniques or the unaided human eye. Accordingly, it is understood that a plurality of first and second colors may be utilized with the present invention. In certain configurations, it may be desirable that the first color be significantly different from the second color such as, for example, a red first color and a contrasting blue second color. However, it is also appreciated herein that more subtle variations in color may be used in accordance with the present invention. For example, the first color may be a lighter hued green and the second color may be a contrasting darker hued green. In other configurations, the first portion 30 and the second portion 32 of the annular skirt portion 14 may form a visually distinct pattern such as, for example, a repeating pattern.

It should be understood that, as used herein, "color" is intended to refer broadly to visually distinguishable characteristics. Accordingly, "color" as used herein refers not only to specific colors of the light spectrum such as red, blue, etc., but also refers to light spectrum colors with textures and/or designs in the surface appearance, such as marble, checkerboard, etc. which may involve more than one light spectrum but which provide visual appearances which may be readily recognized to match the same appearance on a different surface.

When placed on a specimen collection container, the closure 10 of the present invention enables a human observer and/or an automated scanning processor to quickly identify a distinct visual color combination and/or color placement on the closure 10. The color combination and/or color placement may indicate the contents of the specimen collection container and/or the desired testing procedure to be performed on the contents of the specimen collection container to the human observer or automated processor. For example, a hematology specimen may be indicated by a lavender closure having a grey band adjacent the bottom of the annular skirt, whereas a glucose test specimen may be indicated by a grey tube having a yellow band disposed between two grey regions. This is particularly advantageous for specimen collection containers which are processed through a centralized sorting procedure.

In typical specimen collection procedures, an individual specimen collection container is filled with a biological sample for a particular testing procedure. The individual specimen collection container is placed within a rack holder which is typically adapted to receive a plurality of specimen collection containers. Typically, a single rack holder will accommodate specimen collection containers which house different types of specimens, and specimens which will be subjected to different types of testing procedures. For example, a single rack holder may receive a specimen collection container holding a venous blood sample and a specimen collection container holding a capillary blood sample. As each rack holder may house different specimen types or specimens to be tested for different properties, it is necessary to subsequently sort the specimen collection containers for proper processing. In accordance with an embodiment of the present invention, the specimen collection containers are sorted by an automated process in which either the contents or the container or the intended testing procedure to be performed on the contents of the container are identified by the first and second portions 30, 32 of the annular skirt 14 of the closure 10. In one embodiment, each specimen collection container is passed by a computerized scanner which is adapted to recognize color contrast and/or color positioning. In a further embodiment, each specimen collection container is oriented such that the computerized scanner reads the annular skirt 14 of the closure 10 to identify the color contrast and/or color positioning and determine the contents of the specimen collection container and/or the intended testing procedure to be performed on the contents of the specimen collection container. In order to help discern the color contrast and/or color position, each closure 10 may be provided in front of either a white background, as shown in FIGS. 16, 18, 20, 22, 24, 26, 28, 30, 32, 34, 36, 38, 40, 42, 44, 46, 48, 50, 52, 54, and 56, or a dark background, such as a black background, as shown in FIGS. 17, 19, 21, 23, 25, 27, 29, 31, 33, 35, 37, 39, 41, 43, 45, 47, 49, 51, 53, 55, and 57. Accordingly, the color contrast and/or color location of the first and second portions may be selected for optimizing the visual color contrast and/or color locations of the closure 10 specific to the background against which the annular skirt 14 will be viewed.

With reference to FIGS. 16-57, various permutations of dark grey and light grey are shown. It is noted that throughout FIGS. 16-57 the dark grey portions are intended to represent a first portion having any suitable first color as discussed herein, and the light grey portions are intended to represent a second portion having any suitable second color as discussed herein.

In accordance with an embodiment of the present invention, either the first color of the first portion 30 or the second color of the second portion 32 of the closure 10 may be the base color of the closure 10. Similarly, the first portion 30 may be the base material forming the closure 10, and the top surface 12 and the first portion 30 may share the same color. In another embodiment, the second portion 32 may be printed over at least a portion of the first portion 30. Alternatively, the first portion 30 may be printed over at least a portion of the second portion 32. In accordance with another configuration, the first portion 30 and the second portion 32 may be co-formed, such as co-molded. Optionally, the first portion 30 and the second portion 32 may be co-formed of the same material, or the first portion 30 may be formed of a first material and the second portion 32 may be formed of a second material that is different than the first portion, such as two different moldable polymeric materials. Alternatively, the first portion 30 and the second portion 32 may be separately formed and subsequently applied, such as an overlay printing that is adhesively applied to the base material of the annular skirt 14 of the closure 10. It is further intended herein that in certain configurations at least one of the first portion 30 and the second portion 32 may be raised above a portion of the annular skirt 14, to provide a tactile distinction between the first portion 30 and the second portion 32 or a portion of the first portion 30 or the second portion 32 and the annular skirt 14. In other embodiments, at least one of the first portion 30 and the second portion 32 may be recessed below a portion of the annular skirt 14. In a further configuration, at least one of the first portion 30 and the second portion 32 may be etched or knurled to identify further distinguishing features.

Figure 16:
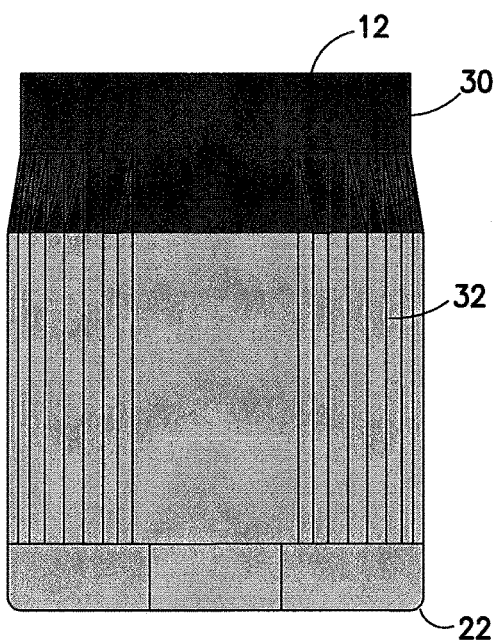
FIG. 16 is a side view of a closure having an annular skirt having a first portion and a second portion adjacent a bottom surface of the annular skirt in accordance with an embodiment of the present invention.
Figure 17:
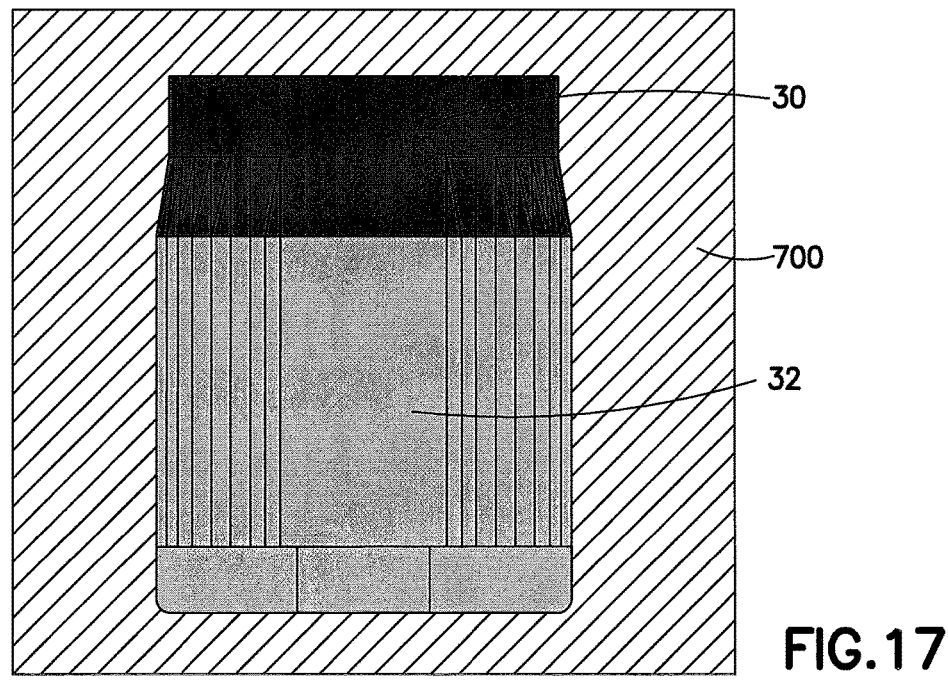
FIG. 17 is a side view of a closure having an annular skirt having a first portion and a second portion adjacent a bottom surface of the annular skirt as shown against a dark imaging background in accordance with an embodiment of the present invention.

With specific reference to FIG. 16, the annular skirt 14, as shown in FIGS. 1-10, may include a first portion 30 formed of a base material having a first color, such as grey, adjacent the top surface 12. A second portion 32 having, for example, a red, yellow, green, blue, light grey, or pink color, may be disposed adjacent a bottom portion 22 of the closure, such as printed over the base material of the closure. The first portion 30 may have a greater surface area, smaller surface area, or equal surface area to that of the second portion 32. As shown in FIG. 16, the closure 10 may be visually identified against a white background. As shown in FIG. 17, the same closure 10 may also be visually identified against a dark background 700.

Figure 18:
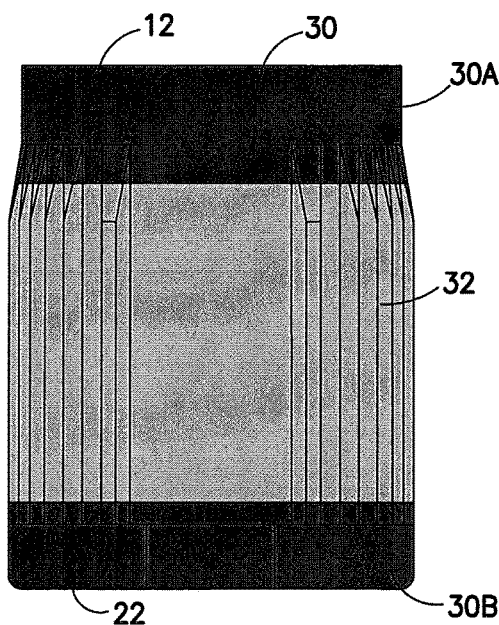
FIG. 18 is a side view of a closure having an annular skirt having a first portion and a second portion disposed between regions of the first portion in accordance with an embodiment of the present invention.
Figure 19:
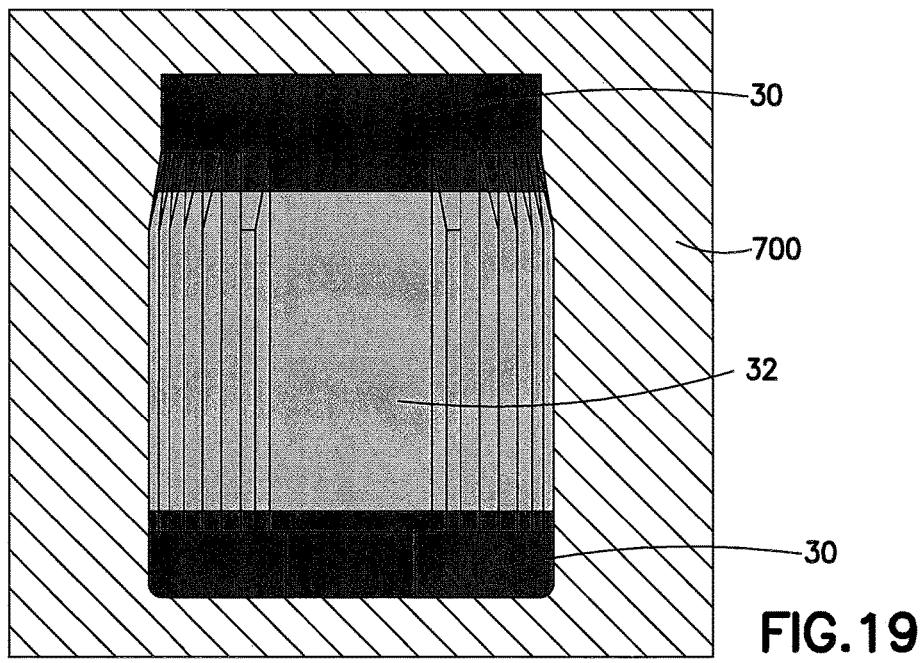
FIG. 19 is a side view of a closure having an annular skirt having a first portion and a second portion disposed between regions of the first portion as shown against a dark imaging background in accordance with an embodiment of the present invention.

With specific reference to FIG. 18, the first portion 30 of the annular skirt 14, as shown in FIGS. 1-10, may include a first region 30A adjacent the top surface 12 of the closure, and a second region 30B adjacent a bottom surface 22 of the closure. The first region 30A and the second region 30B have a first color such as, for example, light blue. The second portion 32 having, for example, a red, yellow, green, blue, light grey, or pink color, may be disposed between the first region 30A and the second region 30B. In one configuration, the second portion 32 may be disposed circumferentially about the annular skirt and may be disposed over the gripping features 20A of the closure as shown in FIGS. 1-10. As shown in FIG. 18, the closure 10 may be visually identified against a white background. As shown in FIG. 19, the same closure 10, may also be visually identified against a dark background 700.

Figure 20:
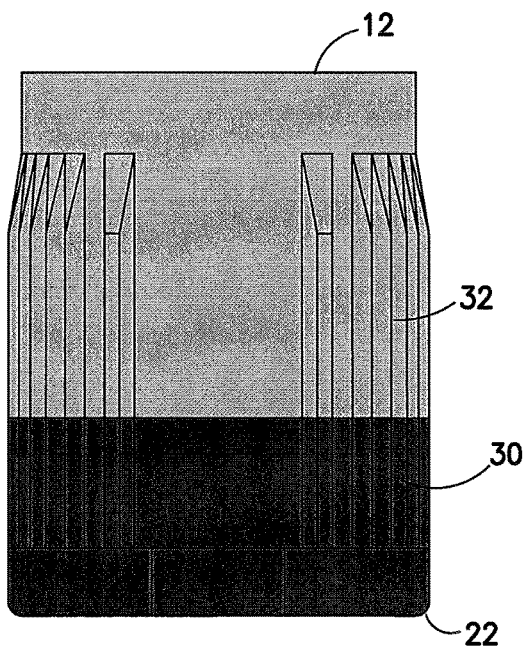
FIG. 20 is a side view of a closure having an annular skirt having a first portion and a second portion disposed adjacent the top surface of the closure in accordance with an embodiment of the present invention.
Figure 21:
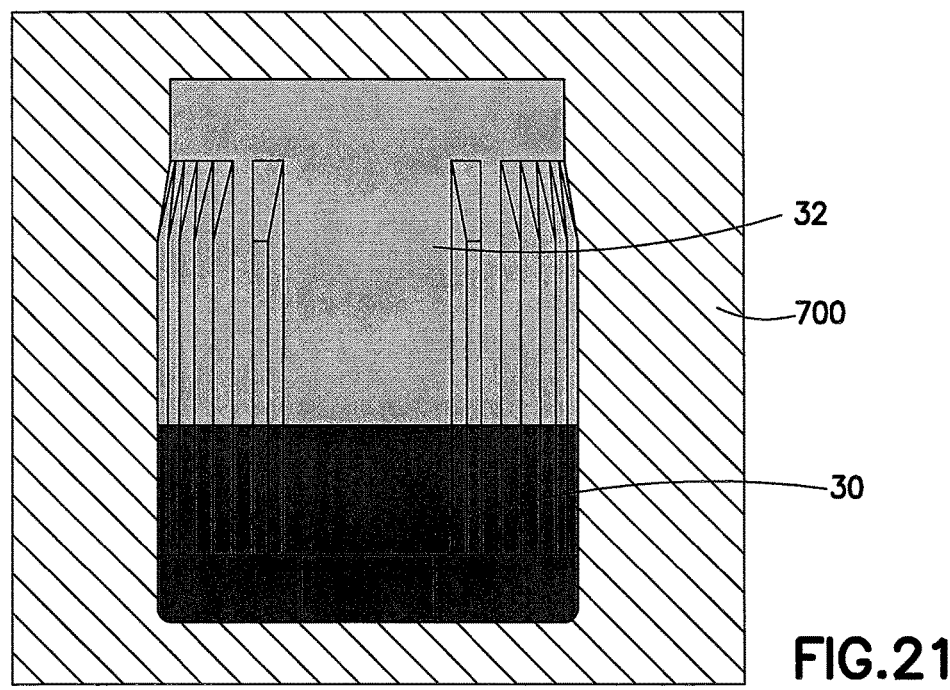
FIG. 21 is a side view of a closure having an annular skirt having a first portion and a second portion disposed adjacent the top surface of the closure as shown against a dark imaging background in accordance with an embodiment of the present invention.

With specific reference to FIG. 20, the annular skirt 14, as shown in FIGS. 1-10, may include a first portion 30 formed of a base material having a first color, such as grey, adjacent the bottom surface 22. A second portion 32 having, for example, a red, yellow, green, blue, light grey, or pink color, may be disposed adjacent a top surface 12 of the closure, such as printed over the base material of the closure. The first portion 30 may have a greater surface area, smaller surface area, or equal surface area to that of the second portion 32. As shown in FIG. 20, the closure 10 may be visually identified against a white background. As shown in FIG. 21, the same closure 10, may also be visually identified against a dark background 700.

Figure 22:
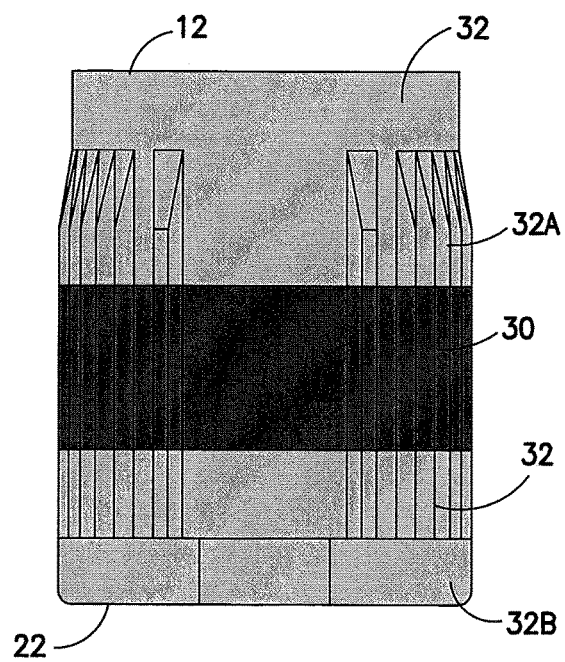
FIG. 22 is a side view of a closure having an annular skirt having a first portion and a second portion disposed between regions of the first portion in accordance with an embodiment of the present invention.
Figure 23:
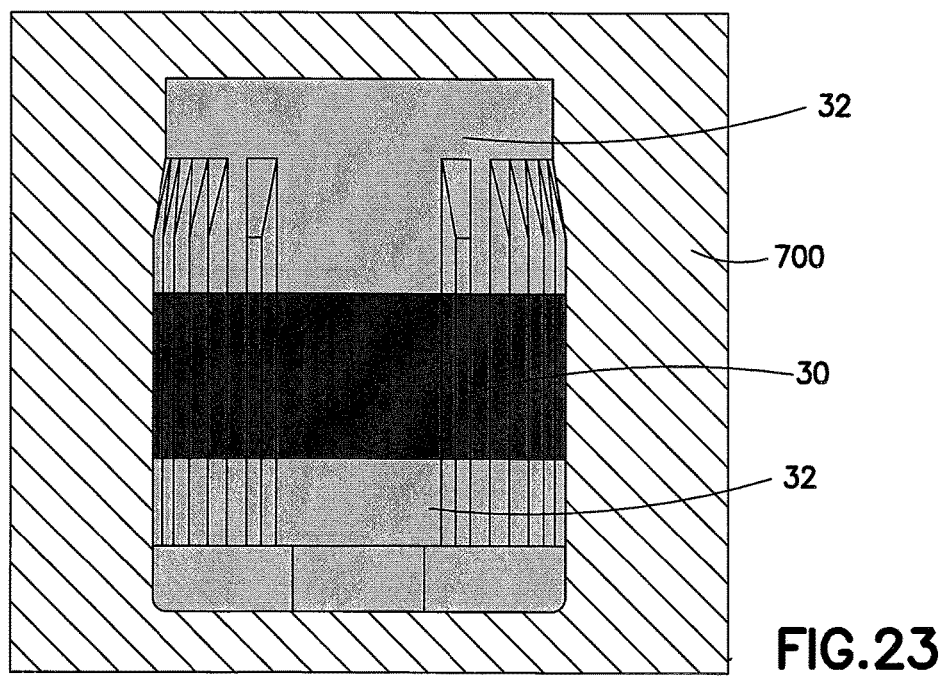
FIG. 23 is a side view of a closure having an annular skirt having a first portion and a second portion disposed between regions of the first portion as shown against a dark imaging background in accordance with an embodiment of the present invention.

With specific reference to FIG. 22, the second portion 32 of the annular skirt 14, as shown in FIGS. 1-10, may include a first region 32A adjacent the top surface 12 of the closure, and a second region 32B adjacent a bottom surface 22 of the closure. The first region 32A and the second region 32B each have a first color such as, for example, red, yellow, green, blue, light grey, or pink color. The first portion 30, having a first color such as white, may be disposed between the first region 32A and the second region 32B. In one configuration, the first portion 30 may be disposed circumferentially about the annular skirt 14 and may be disposed over the gripping features 20A of the closure as shown in FIGS. 1-10. As shown in FIG. 22, the closure 10 may be visually identified against a white background. As shown in FIG. 23, the same closure 10, may also be visually identified against a dark background 700.

Figure 24:
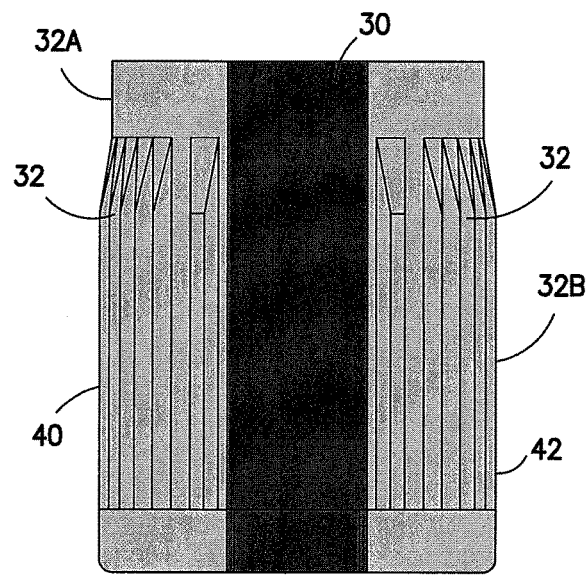
FIG. 24 is a side view of a closure having an annular skirt having a first portion and a second portion disposed between regions of the first portion in accordance with an embodiment of the present invention.
Figure 25:
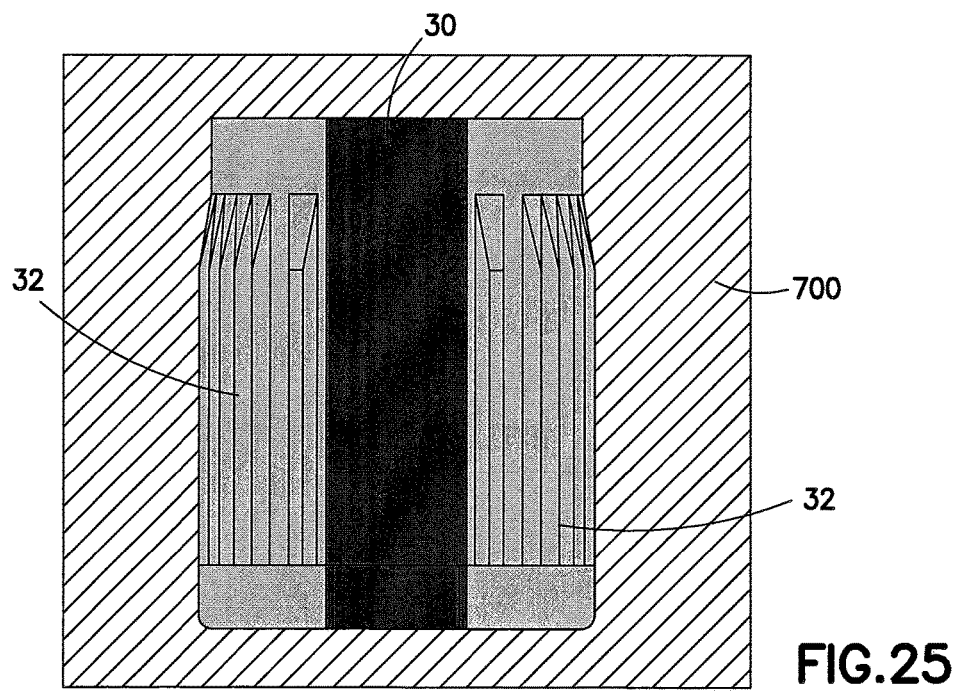
FIG. 25 is a side view of a closure having an annular skirt having a first portion and a second portion disposed between regions of the first portion as shown against a dark imaging background in accordance with an embodiment of the present invention.

With specific reference to FIG. 24, the second portion 32 of the annular skirt 14, as shown in FIGS. 1-10, may include a first region 32A disposed adjacent a first depending sidewall 40 and a second region 32B adjacent a second depending sidewall 42. The first region 32A and the second region 32B have a first color such as, for example, red, yellow, green, blue, light grey, or pink color. The first portion 30, having a first color such as blue, may be disposed between the first region 32A and the second region 32B. In one configuration, the first portion 30 may be disposed on opposing sides of the annular skirt. In another configuration, the first portion 30 may be disposed in segmented bands about the annular skirt. In yet another configuration, the first portion 30 may be continuously disposed between opposing sides of the annular skirt and across the top surface, as shown in FIGS. 1-10. As shown in FIG. 24, the closure 10 may be visually identified against a white background. As shown in FIG. 25, the same closure 10 may also be visually identified against a dark background 700.

Figure 26:
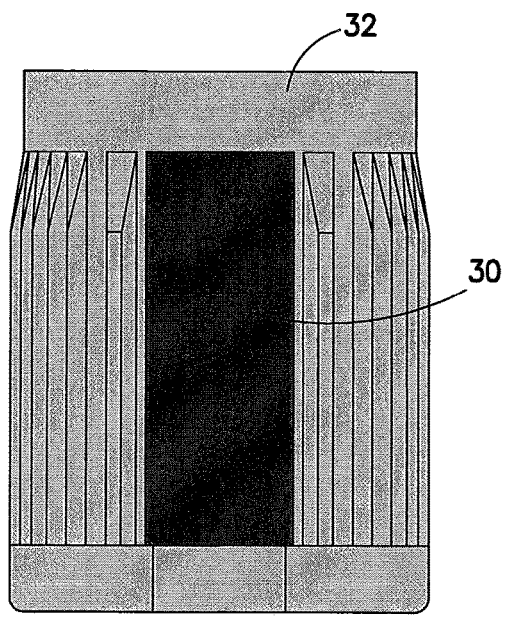
FIG. 26 is a side view of a closure having an annular skirt having a first portion and a second portion surrounding the first portion in accordance with an embodiment of the present invention.
Figure 27:
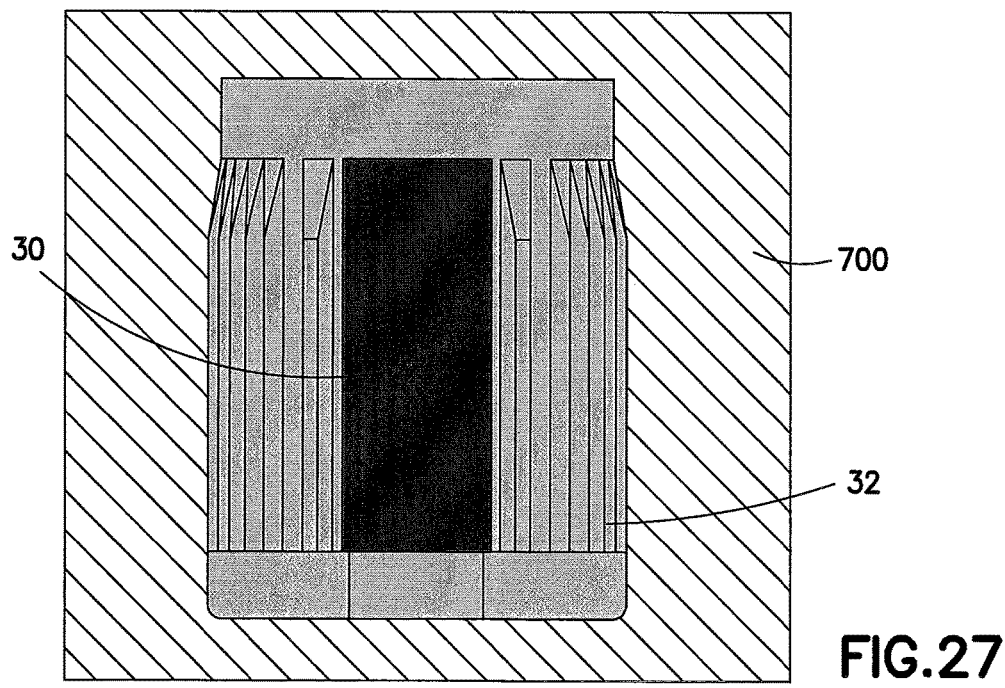
FIG. 27 is a side view of a closure having an annular skirt having a first portion and a second portion surrounding the first portion as shown against a dark imaging background in accordance with an embodiment of the present invention.
Figure 28:
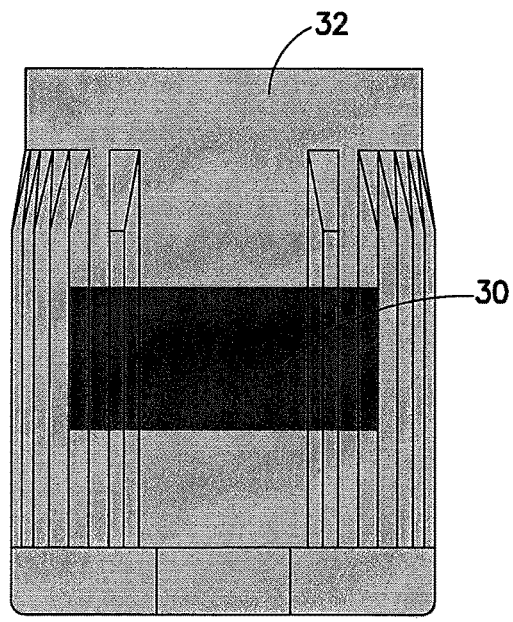
FIG. 28 is a side view of a closure having an annular skirt having a first portion and a second portion surrounding the first portion in accordance with an embodiment of the present invention.
Figure 29:
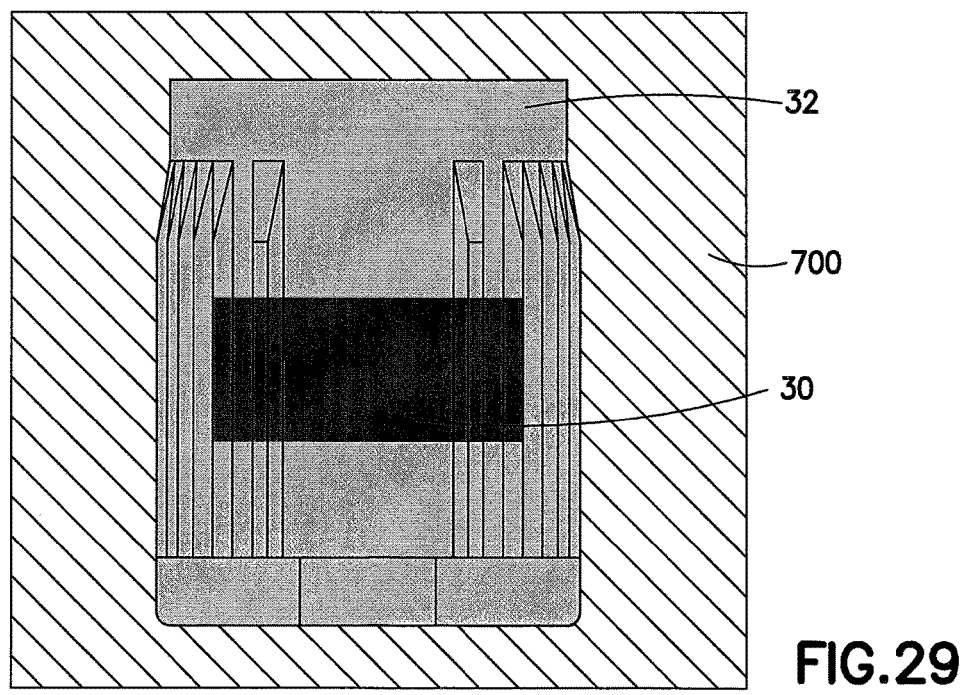
FIG. 29 is a side view of a closure having an annular skirt having a first portion and a second portion surrounding the first portion as shown against a dark imaging background in accordance with an embodiment of the present invention.

With specific reference to FIGS. 26 and 28, the first portion 30 may be surrounded by the second portion 32. As shown specifically in FIG. 26, the first portion 30 has a first color, for example blue, and the second portion 32 has a second color such as, for example, red, yellow, green, blue, light grey, or pink color. The first portion 30 may have any shape, such as a longitudinally oriented rectangular configuration, as shown in FIG. 26, or a horizontally oriented rectangular configuration, as shown in FIG. 28. It is anticipated herein, that the first portion 30 may have any shape surrounded by the second portion 32. As shown in FIGS. 26 and 28, the closures 10 may be visually identified against a white background. As shown in FIGS. 27 and 29, the same closures 10 may also be visually identified against a dark background 700.

Figure 30:
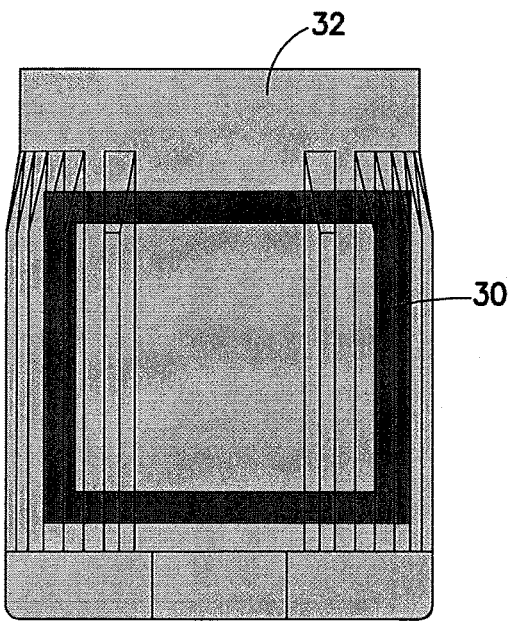
FIG. 30 is a side view of a closure having an annular skirt having a first portion and a second portion disposed between two regions of the first portion in accordance with an embodiment of the present invention.
Figure 31:
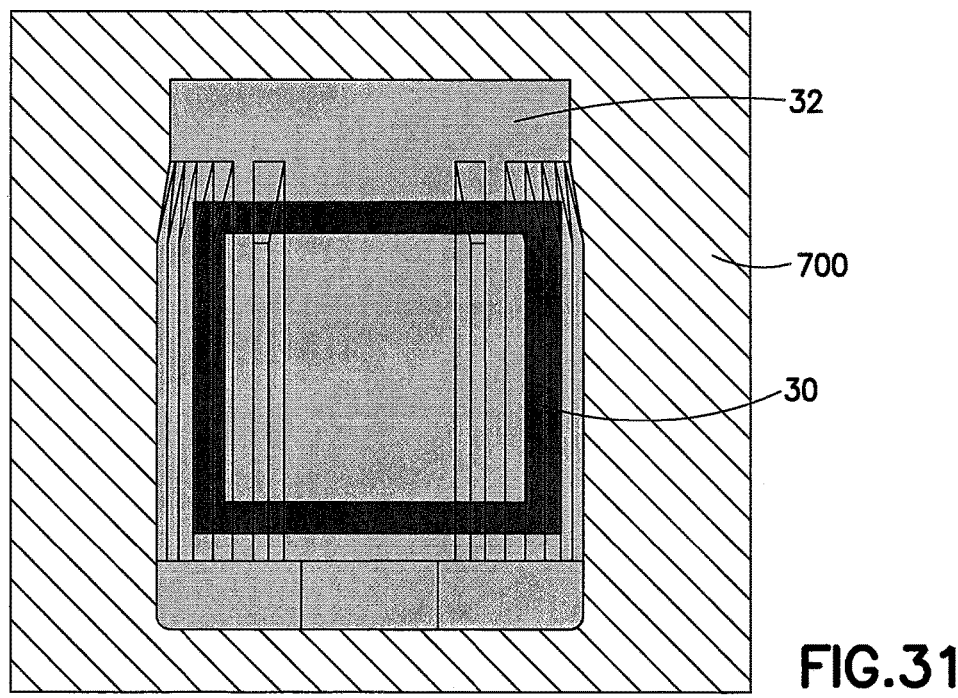
FIG. 31 is a side view of a closure having an annular skirt having a first portion and a second portion disposed between two regions of the first portion as shown against a dark imaging background in accordance with an embodiment of the present invention.

With specific reference to FIG. 30, the first portion 30 may be surrounded by the second portion 32, as similarly described above with reference to FIGS. 26 and 28. In this configuration, the second portion 32 may be applied over the first portion 30 or, alternatively, the second portion may be applied as two separated regions over the first portion 30, such as by printing and/or stamping. As shown in FIG. 30, the closure 10 may be visually identified against a white background. As shown in FIG. 31, the same closure 10 may also be visually identified against a dark background 700.

Figure 32:
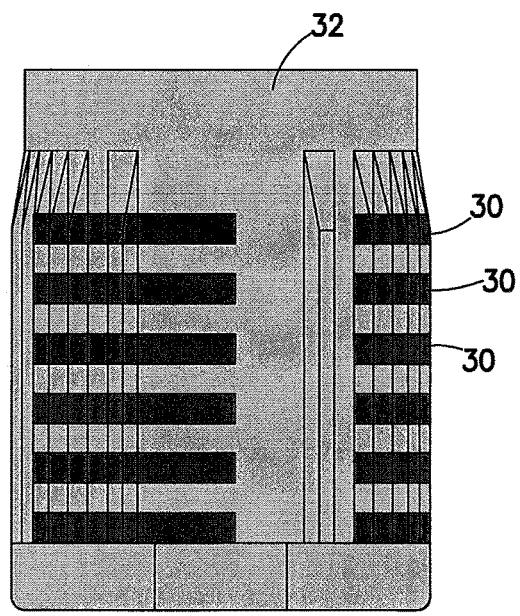
FIG. 32 is a side view of a closure having an annular skirt having a first portion and a second portion in which the first portion and the second portion form a repeating pattern in accordance with an embodiment of the present invention.
Figure 33:
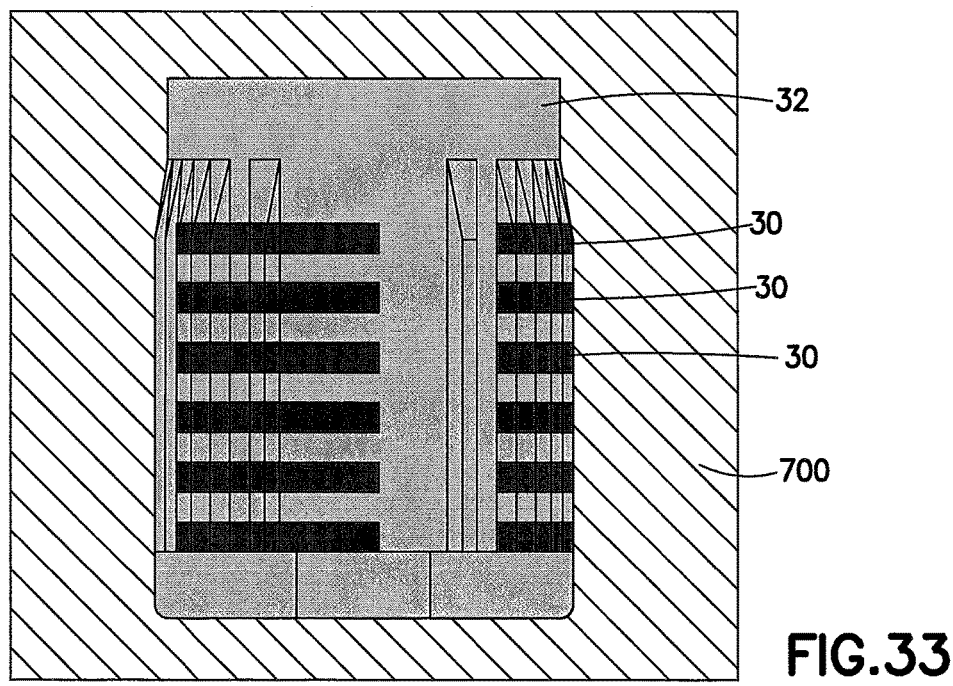
FIG. 33 is a side view of a closure having an annular skirt having a first portion and a second portion in which the first portion and the second portion form a repeating pattern as shown against a dark imaging background in accordance with an embodiment of the present invention.
Figure 34:
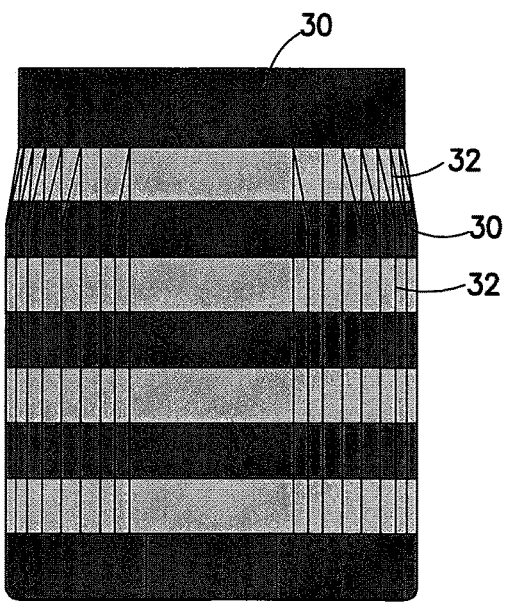
FIG. 34 is a side view of a closure having an annular skirt having a first portion and a second portion in which the first portion and the second portion form a repeating pattern in accordance with an embodiment of the present invention.
Figure 35:
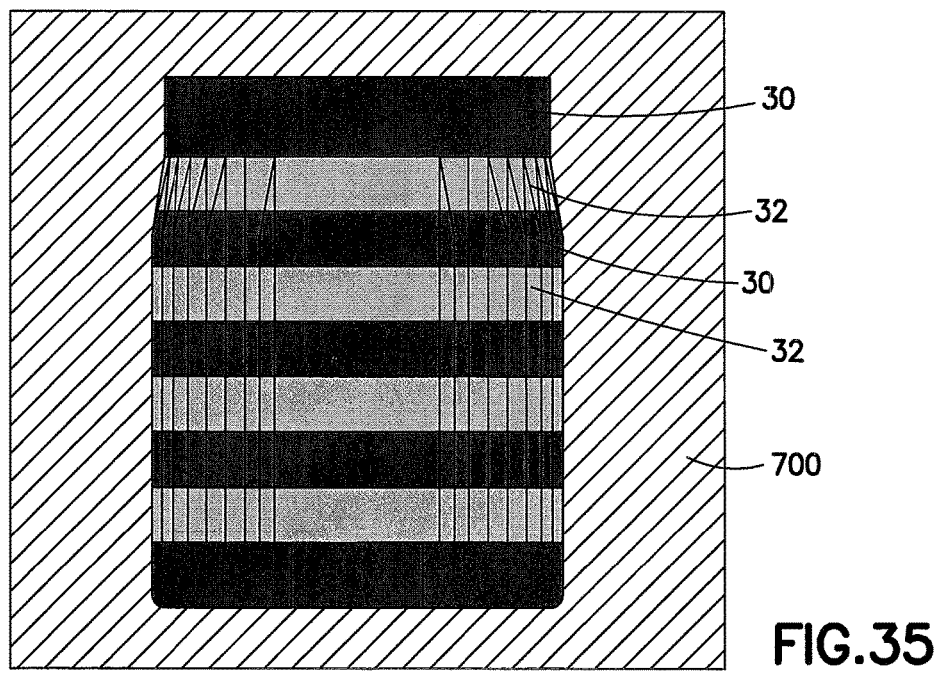
FIG. 35 is a side view of a closure having an annular skirt having a first portion and a second portion in which the first portion and the second portion form a repeating pattern as shown against a dark imaging background in accordance with an embodiment of the present invention.
Figure 36:
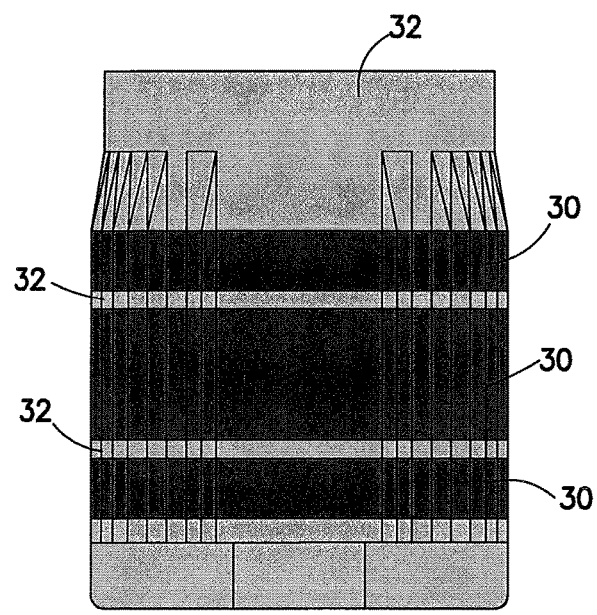
FIG. 36 is a side view of a closure having an annular skirt having a first portion and a second portion in which the first portion and the second portion form a repeating pattern in accordance with an embodiment of the present invention.
Figure 37:
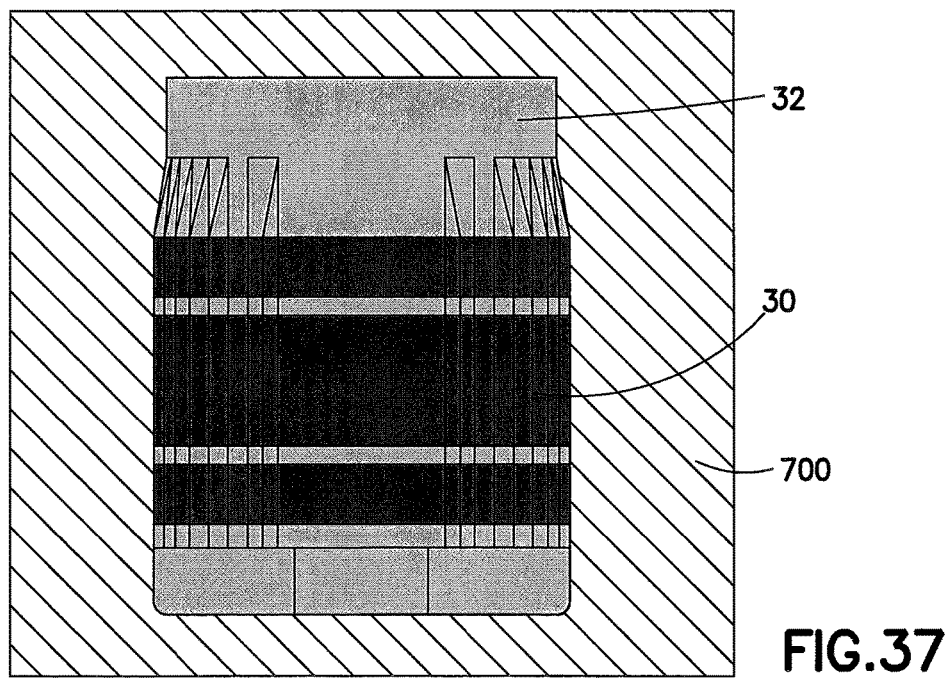
FIG. 37 is a side view of a closure having an annular skirt having a first portion and a second portion in which the first portion and the second portion form a repeating pattern as shown against a dark imaging background in accordance with an embodiment of the present invention.

With specific reference to FIGS. 32-37, the first portion 30 and the second portion 32 may form a repeating pattern about at least a portion of the annular skirt. In one configuration, the repeating pattern may be formed by a plurality of regions of the first portion 30 disposed adjacent a plurality of regions of the second portion 32. These regions may be segmented, as shown in FIGS. 32-33, or continuous as shown in FIGS. 34-37. In one configuration, the regions of the first portion 30 may be evenly spaced between the regions of the second portion 32, as shown in FIGS. 32-33. In another configuration, the regions of the first portion 30 and the regions of the second portion 32 are unevenly spaced. As shown in FIGS. 32, 34 and 36, the closures 10 may be visually identified against a white background. As shown in FIGS. 33, 35 and 37, the same closures 10 may also be visually identified against a dark background 700.

Figure 38:
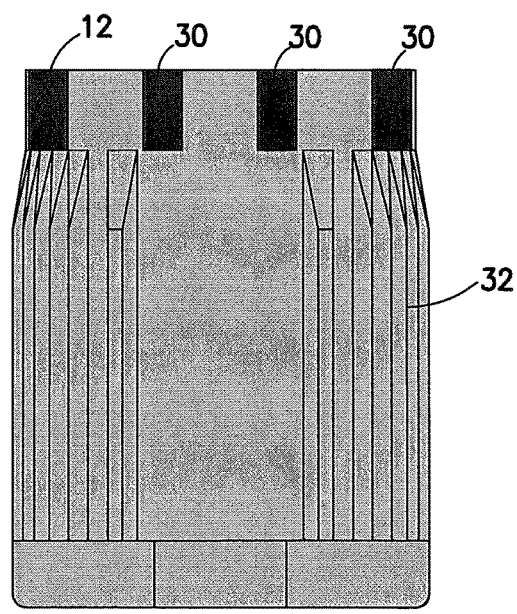
FIG. 38 is a side view of a closure having an annular skirt having a first portion and a second portion in which the first portion and the second portion form a repeating pattern disposed adjacent the top surface in accordance with an embodiment of the present invention.
Figure 39:
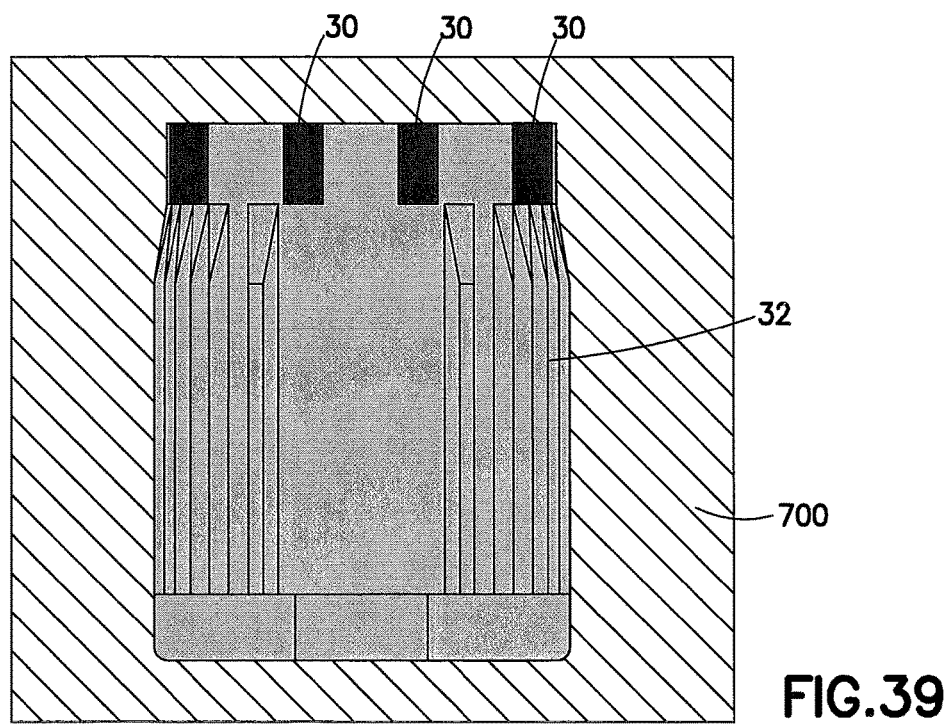
FIG. 39 is a side view of a closure having an annular skirt having a first portion and a second portion in which the first portion and the second portion form a repeating pattern disposed adjacent the top surface as shown against a dark imaging background in accordance with an embodiment of the present invention.
Figure 40:
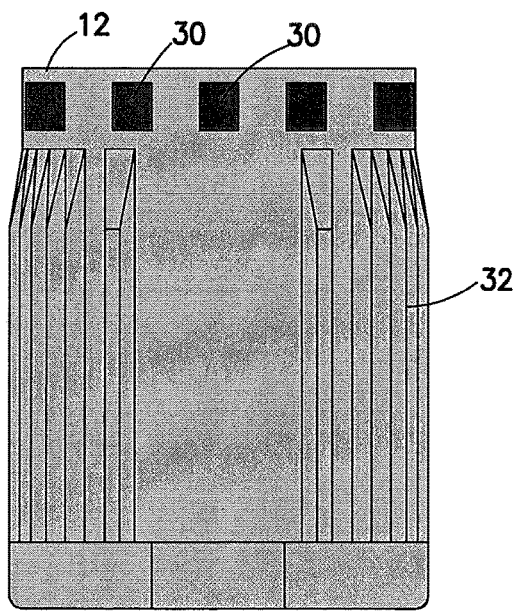
FIG. 40 is a side view of a closure having an annular skirt having a first portion and a second portion in which the first portion and the second portion form a repeating pattern disposed adjacent the top surface of the closure in accordance with an embodiment of the present invention.
Figure 41:
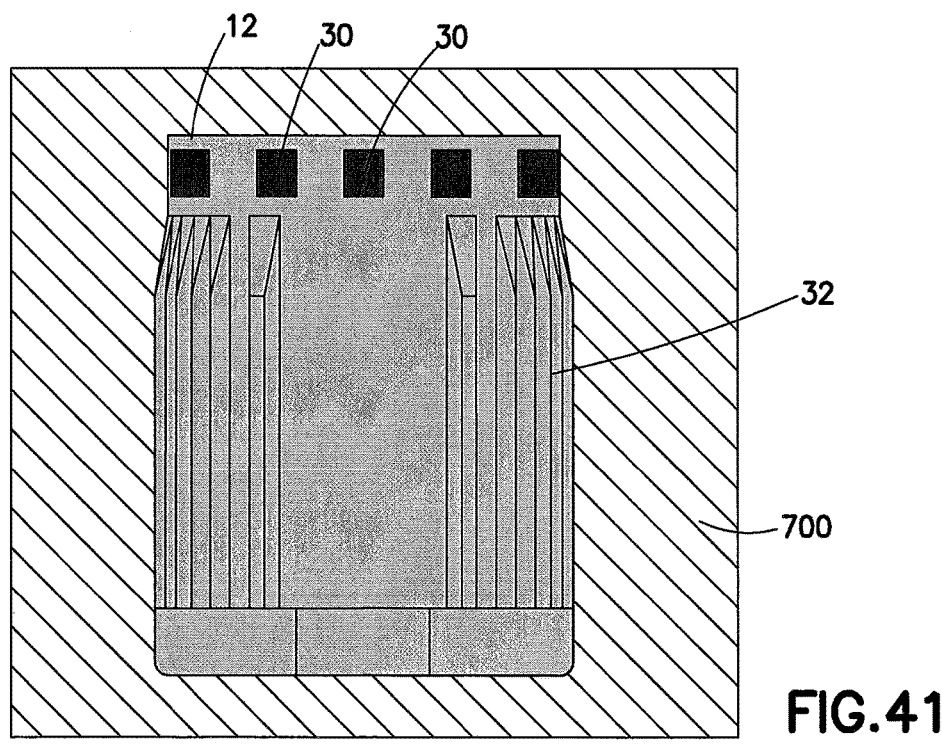
FIG. 41 is a side view of a closure having an annular skirt having a first portion and a second portion in which the first portion and the second portion form a repeating pattern disposed adjacent the top surface of the closure as shown against a dark imaging background in accordance with an embodiment of the present invention.
Figure 48:
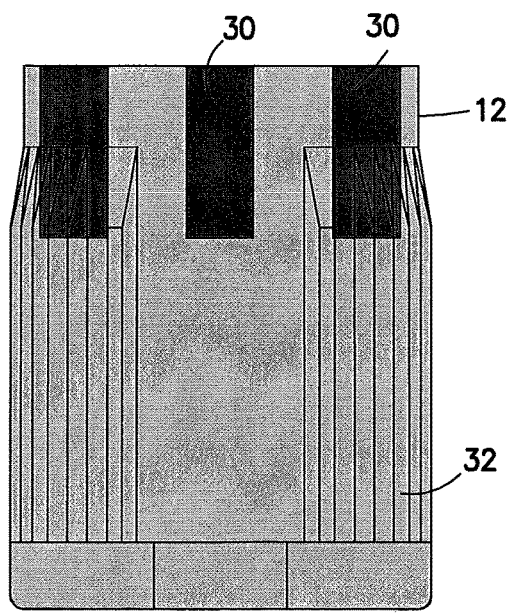
FIG. 48 is a side view of a closure having an annular skirt having a first portion and a second portion in which the first portion and the second portion form a repeating pattern disposed adjacent the top surface of the closure in accordance with an embodiment of the present invention.
Figure 49:
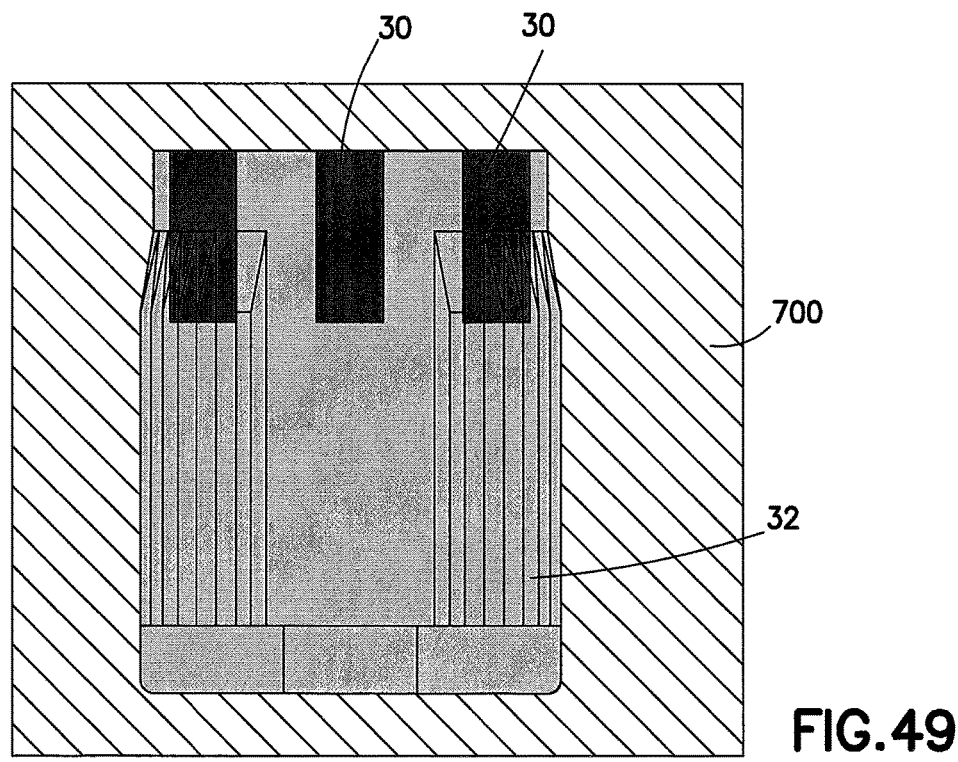
FIG. 49 is a side view of a closure having an annular skirt having a first portion and a second portion in which the first portion and the second portion form a repeating pattern disposed adjacent the top surface of the closure as shown against a dark imaging background in accordance with an embodiment of the present invention.
Figure 50:
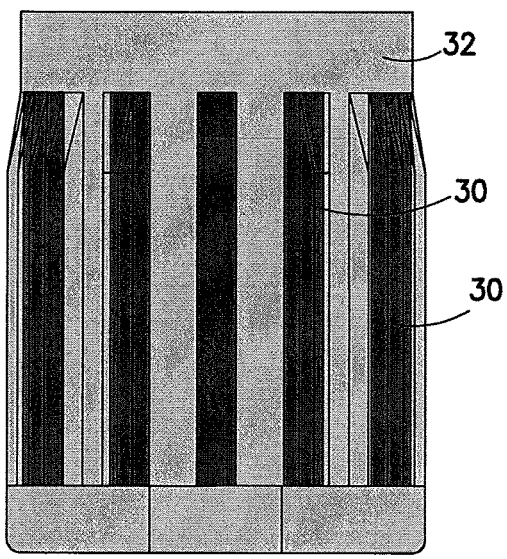
FIG. 50 is a side view of a closure having an annular skirt having a first portion and a second portion in which the first portion and the second portion form a repeating pattern in accordance with an embodiment of the present invention.
Figure 51:
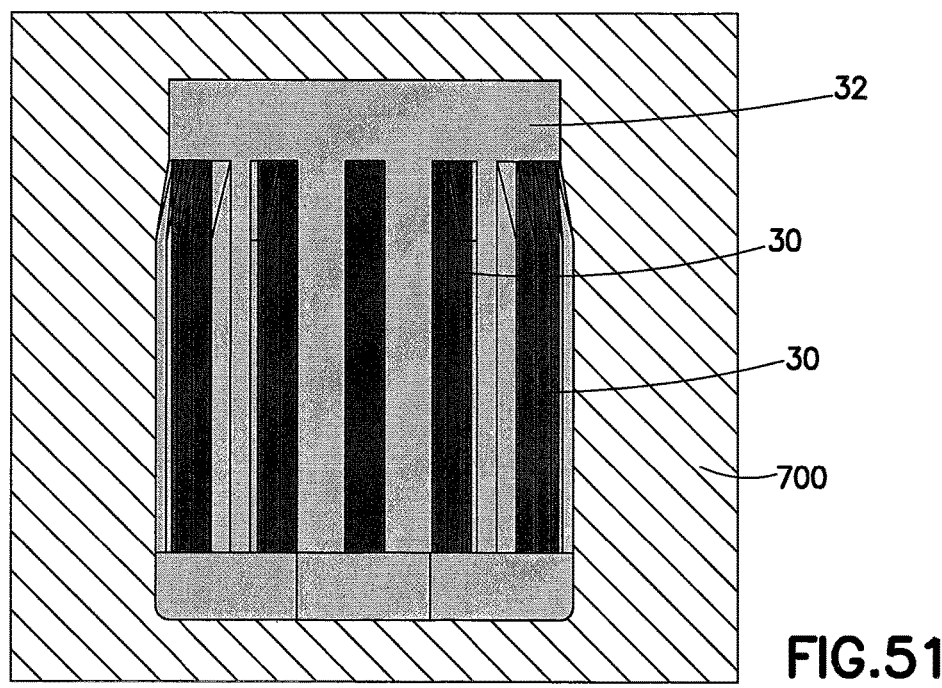
FIG. 51 is a side view of a closure having an annular skirt having a first portion and a second portion in which the first portion and the second portion form a repeating pattern as shown against a dark imaging background in accordance with an embodiment of the present invention.
Figure 52:
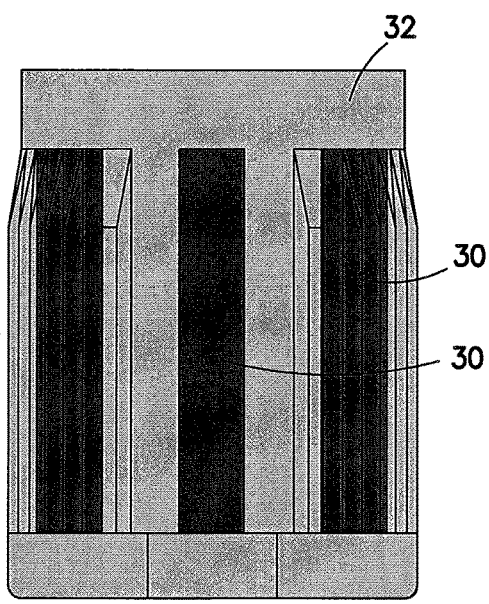
FIG. 52 is a side view of a closure having an annular skirt having a first portion and a second portion in which the first portion and the second portion form a repeating pattern in accordance with an embodiment of the present invention.
Figure 53:
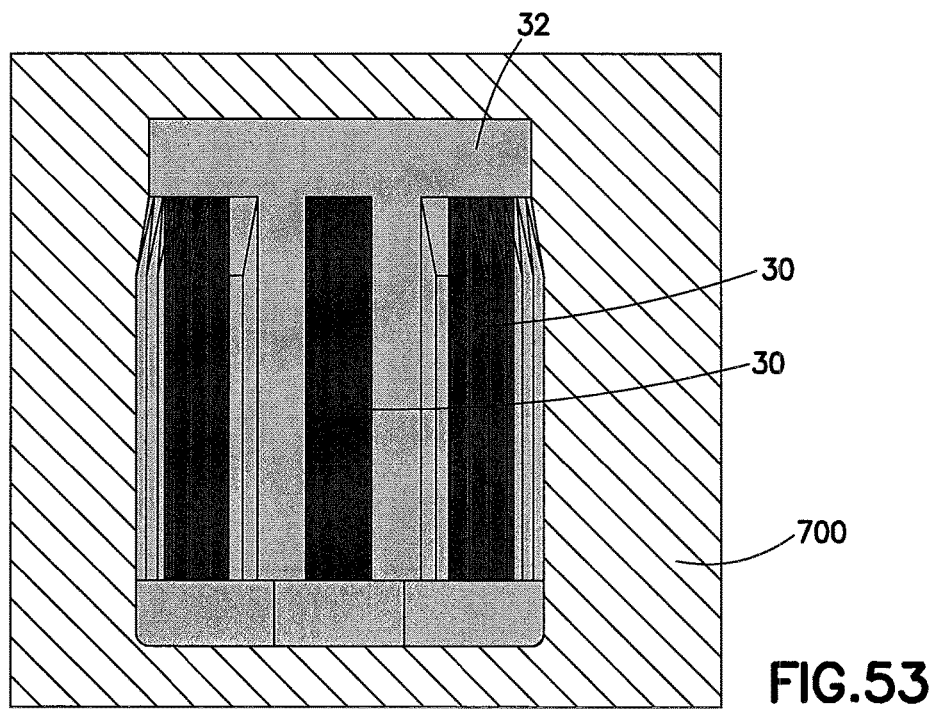
FIG. 53 is a side view of a closure having an annular skirt having a first portion and a second portion in which the first portion and the second portion form a repeating pattern as shown against a dark imaging background in accordance with an embodiment of the present invention.
Figure 54:
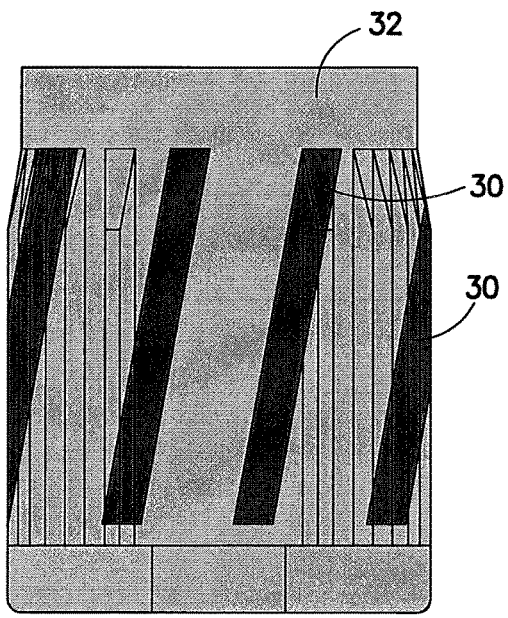
FIG. 54 is a side view of a closure having an annular skirt having a first portion and a second portion in which the first portion and the second portion form a repeating pattern in accordance with an embodiment of the present invention.
Figure 55:
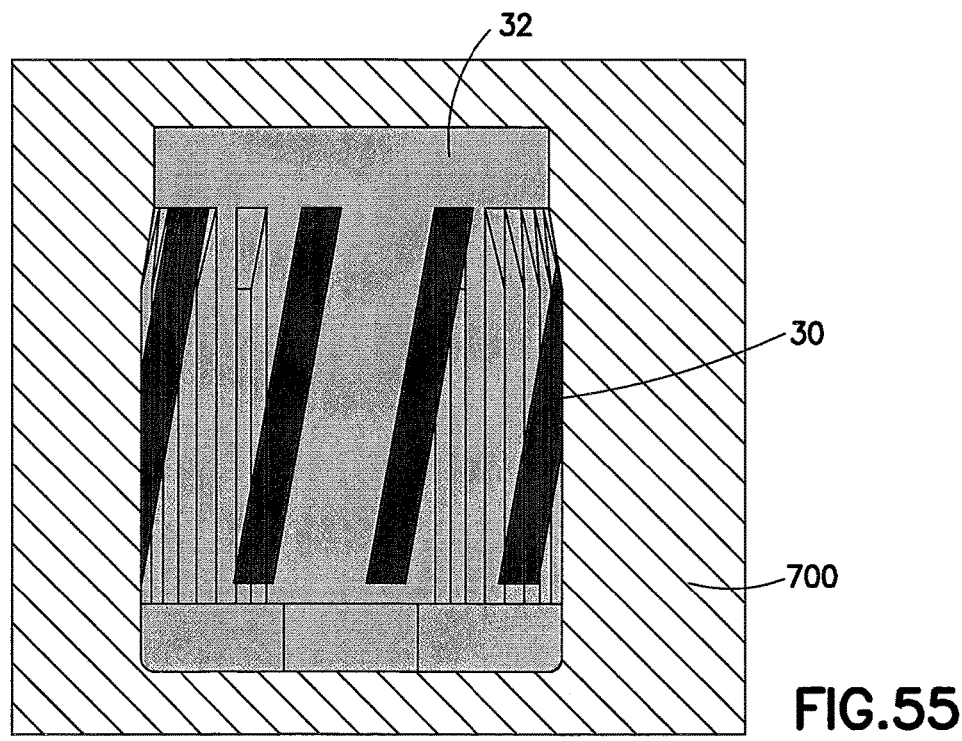
FIG. 55 is a side view of a closure having an annular skirt having a first portion and a second portion in which the first portion and the second portion form a repeating pattern as shown against a dark imaging background in accordance with an embodiment of the present invention.
Figure 56:
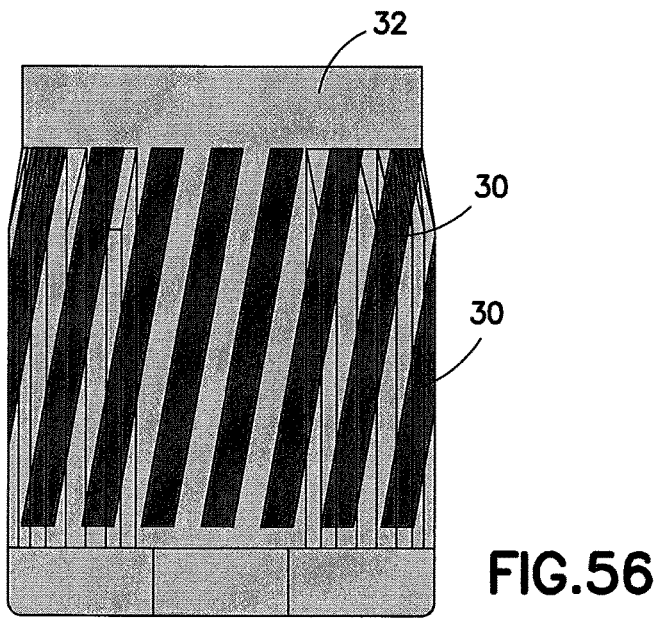
FIG. 56 is a side view of a closure having an annular skirt having a first portion and a second portion in which the first portion and the second portion form a repeating pattern in accordance with an embodiment of the present invention.
Figure 57:
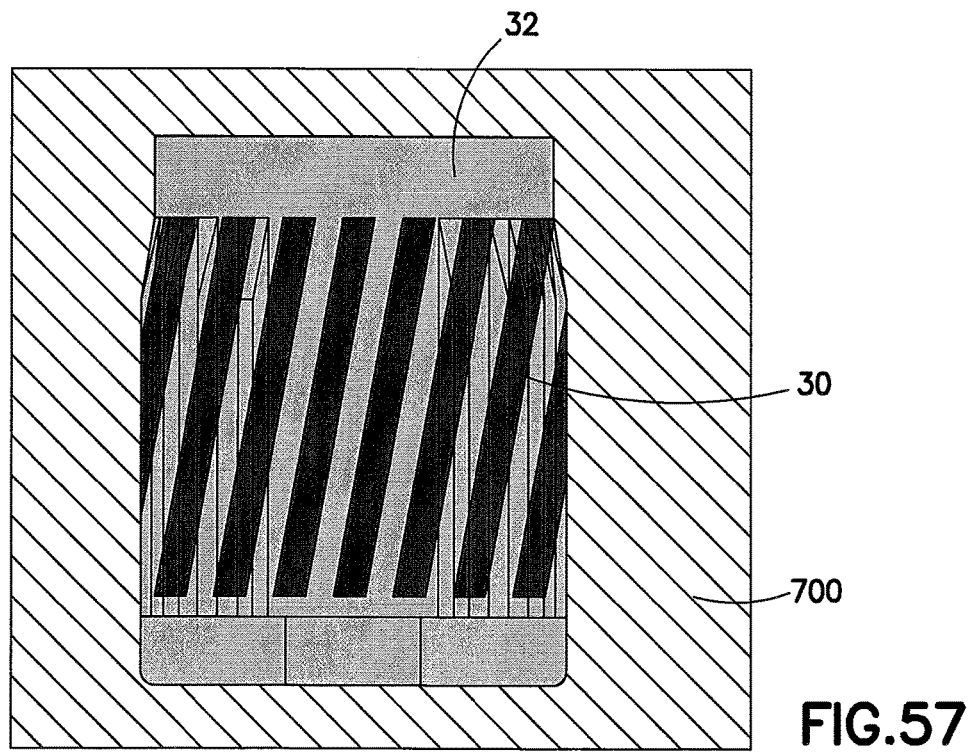
FIG. 57 is a side view of a closure having an annular skirt having a first portion and a second portion in which the first portion and the second portion form a repeating pattern as shown against a dark imaging background in accordance with an embodiment of the present invention.

With specific reference to FIGS. 38-41 and 48-49, the first portion 30 and the second portion 32 may form a repeating pattern about a selected portion of the annular skirt, such as adjacent the top surface 12. As shown specifically in FIGS. 38-39 and FIGS. 48-49, the repeating pattern may extend into the top surface 12. Alternatively, as shown in FIGS. 40-41, the repeating pattern may be formed by regions of the first portion 30 that are fully surrounded by the second portion 32 positioned adjacent the top surface 12. As shown in FIGS. 38, 40, and 48, the closures 10 may be visually identified against a white background. As shown in FIGS. 39, 41, and 49, the same closures 10 may also be visually identified against a dark background 700.

Figure 42:
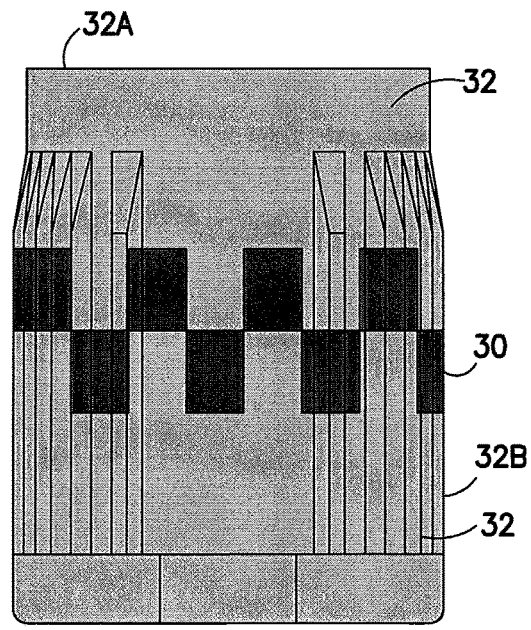
FIG. 42 is a side view of a closure having an annular skirt having a first portion and a second portion disposed between two regions of the first portion in accordance with an embodiment of the present invention.
Figure 43:
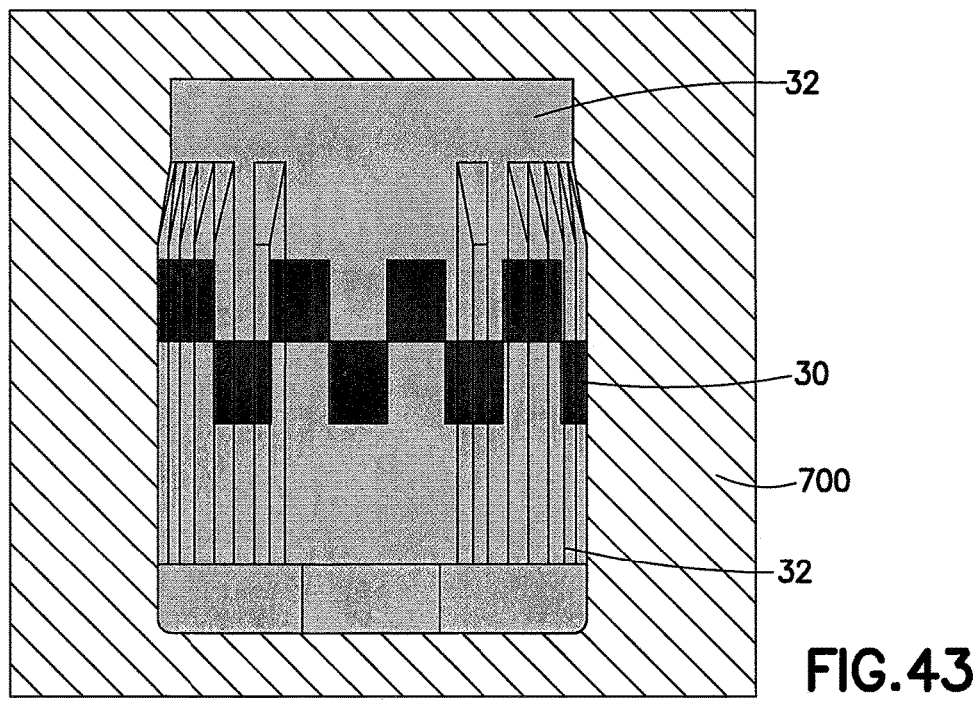
FIG. 43 is a side view of a closure having an annular skirt having a first portion and a second portion disposed between two regions of the first portion as shown against a dark imaging background in accordance with an embodiment of the present invention.
Figure 44:
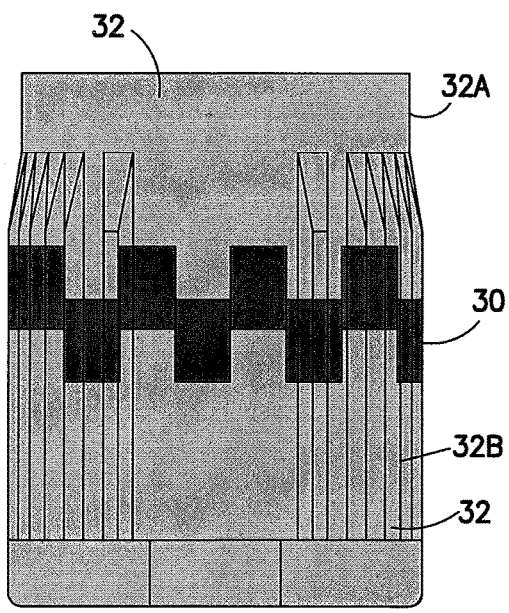
FIG. 44 is a side view of a closure having an annular skirt having a first portion and a second portion disposed between two regions of the first portion in accordance with an embodiment of the present invention.
Figure 45:
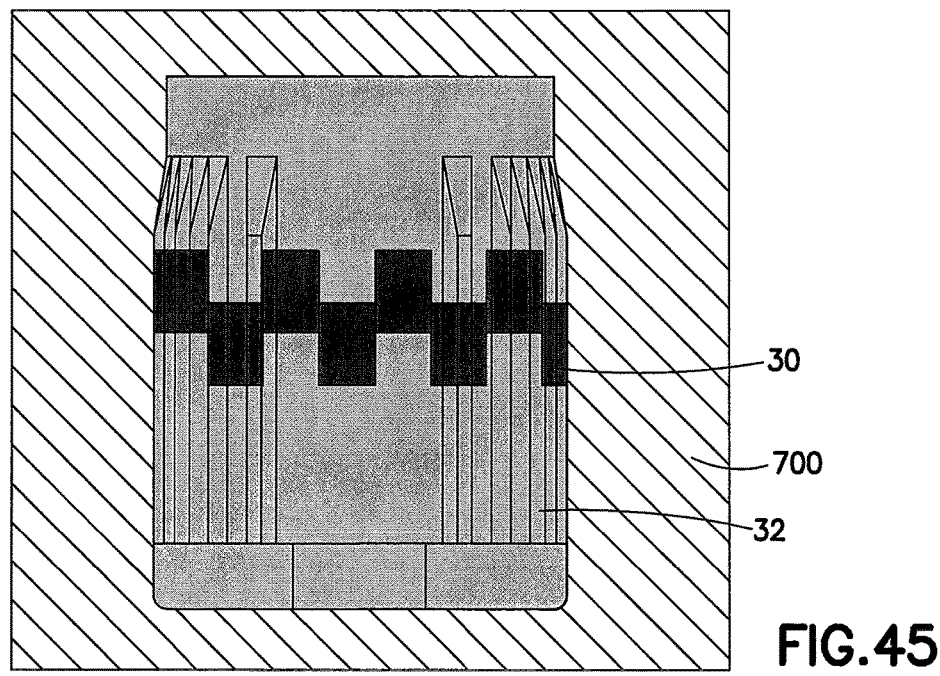
FIG. 45 is a side view of a closure having an annular skirt having a first portion and a second portion disposed between two regions of the first portion as shown against a dark imaging background in accordance with an embodiment of the present invention.

With specific reference to FIGS. 42-45, the first portion 30 may form a repeating pattern that is fully surrounded and defined by a first region 32A of the second portion 32 and a second region 32B of the second portion 32. As shown in FIGS. 42-45, the repeating pattern may be disposed at any location, such as circumferentially disposed about the annular skirt. As shown in FIGS. 42 and 44, the closures 10 may be visually identified against a white background. As shown in FIGS. 43 and 45, the same closures 10 may also be visually identified against a dark background 700.

Figure 46:
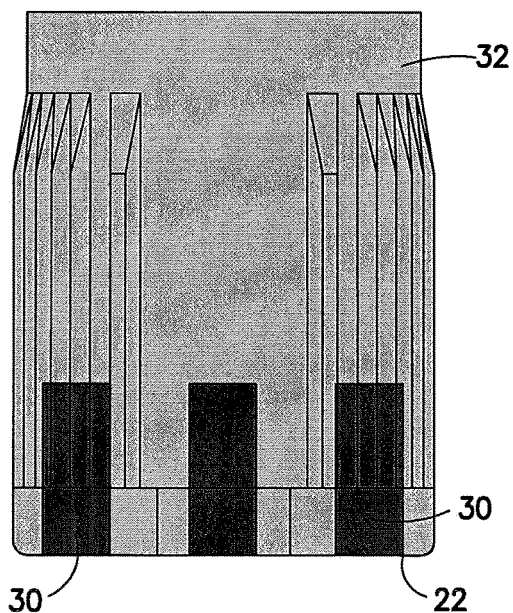
FIG. 46 is a side view of a closure having an annular skirt having a first portion and a second portion in which the first portion and the second portion form a repeating pattern disposed adjacent the bottom surface of the closure in accordance with an embodiment of the present invention.
Figure 47:
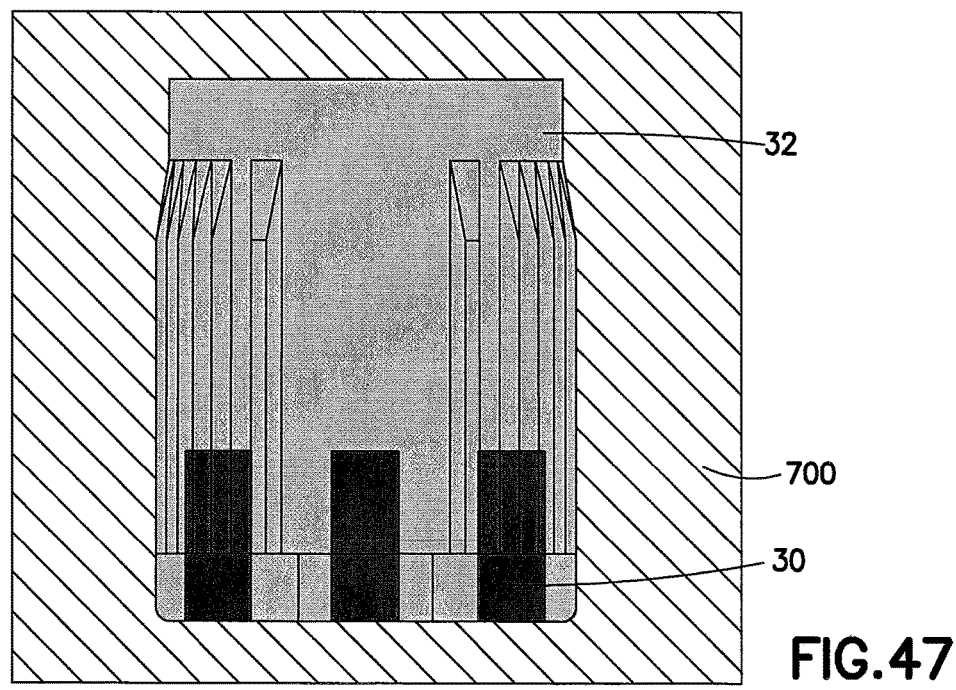
FIG. 47 is a side view of a closure having an annular skirt having a first portion and a second portion in which the first portion and the second portion form a repeating pattern disposed adjacent the bottom surface of the closure as shown against a dark imaging background in accordance with an embodiment of the present invention.

With specific reference to FIGS. 46-47, the first portion 30 and the second portion 32 may form a repeating pattern about a selected portion of the annular skirt, such as adjacent the bottom surface 22. As shown specifically in FIGS. 46-47, the repeating pattern may extend into the bottom surface 22. Alternatively, the repeating pattern may be formed by regions of the first portion 30 that are fully surrounded by the second portion 32 positioned adjacent the bottom surface 22. As shown in FIG. 46, the closure 10 may be visually identified against a white background. As shown in FIG. 47, the same closure 10 may also be visually identified against a dark background 700.

With specific reference to FIGS. 50-53, the first portion 30 and the second portion 32 may form a repeating pattern about a selected portion of the annular skirt. In one configuration, the repeating pattern may be disposed over the gripping portions 20A as shown in FIGS. 1-10. As shown specifically in FIGS. 50-53, the repeating pattern may be formed by regions of the first portion 30 that are fully surrounded by the second portion 32. In one configuration, the regions of the first portion 30 form vertical bands about the annular skirt of the closure. Alternatively, as shown in FIGS. 54-57, the repeating pattern may be formed by diagonally disposed regions of the first portion 30 that are fully surrounded by corresponding diagonally disposed regions of the second portion 32. As shown in FIGS. 50, 52, 54, and 56, the closures 10 may be visually identified against a white background. As shown in FIGS. 51, 53, 55, and 57, the same closures 10 may also be visually identified against a dark background 700.

In certain configurations, with reference to FIGS. 16-57, the first portion 30 and the second portion 32 may be variations in hue, tint, brightness, intensity, or finish of the same color. For example, the first portion 30 has a light red color whereas the second portion 32 has a dark red color. The color combinations and color locations as described above may be applicable to any first portion 30 and second portion 32 having varying hue, tint, brightness, intensity, or finish.

Color combinations and/or color locations and/or color patterning present on the annular skirt 14 of the closure 10 may be used to indicate the intended sample analysis of a specimen collection container, such as clinical chemistry, hematology, or immunochemistry/immunoassay. It is noted that in many automated processing systems, front end automated processes are often employed to prepare a specimen for proper analysis. Specific color combinations and/or color locations and/or color patterning present on the annular skirt 14 of the closure 10 may also indicate intended front end automation, such as sorting specimen collection containers by type and/or contents, accessorizing specimen collection containers superficially or with additives specific to the contents of the specimen collection container, centrifugation, serum level analysis, decapping, aliquoting, and automated labeling of secondary tubes. In other automated processing systems, back end automated processes are often employed after a specimen is analyzed. Specific color combinations and/or color locations and/or color patterning present on the annular skirt 14 of the closure 10 may indicate back end automation, such as resealing, storage, and retrieval.

It is noted herein, that certain color combinations and/or color locations present on the annular skirt 14 of the closure 10 may also be used to indicate whether a specimen collection container includes a region adapted for instrument compatibility, such as a false bottom region. Alternatively, certain color combinations and/or color locations present on the annular skirt 14 of the closure 10 may be used to indicate specimen collection containers having large volume exterior dimensions, such as that of a standard 16 mm tube, with a reduced volume interior. Providing a visual identification of such tubes may reduce instrument incompatibility and reduce instances of system errors that require user intervention by bypassing an automation processing step for which the specimen collection container is not compatible. For example, a specimen collection container that is not compatible for aliqouting, resealing, or serum detection level analysis may require human intervention if it is improperly indicated by an automated processing system as requiring such a processing step. The presence of certain visual features, such as color locations, may also allow for certain automatic functions to be bypassed. For example, in an automated specimen collection container directing process, certain specimen collection containers that do not require certain pretreatments or other processing steps may bypass these actions, whereas other specimen collection containers requiring the pretreatment may be directed to the appropriate action.

Figure 58:
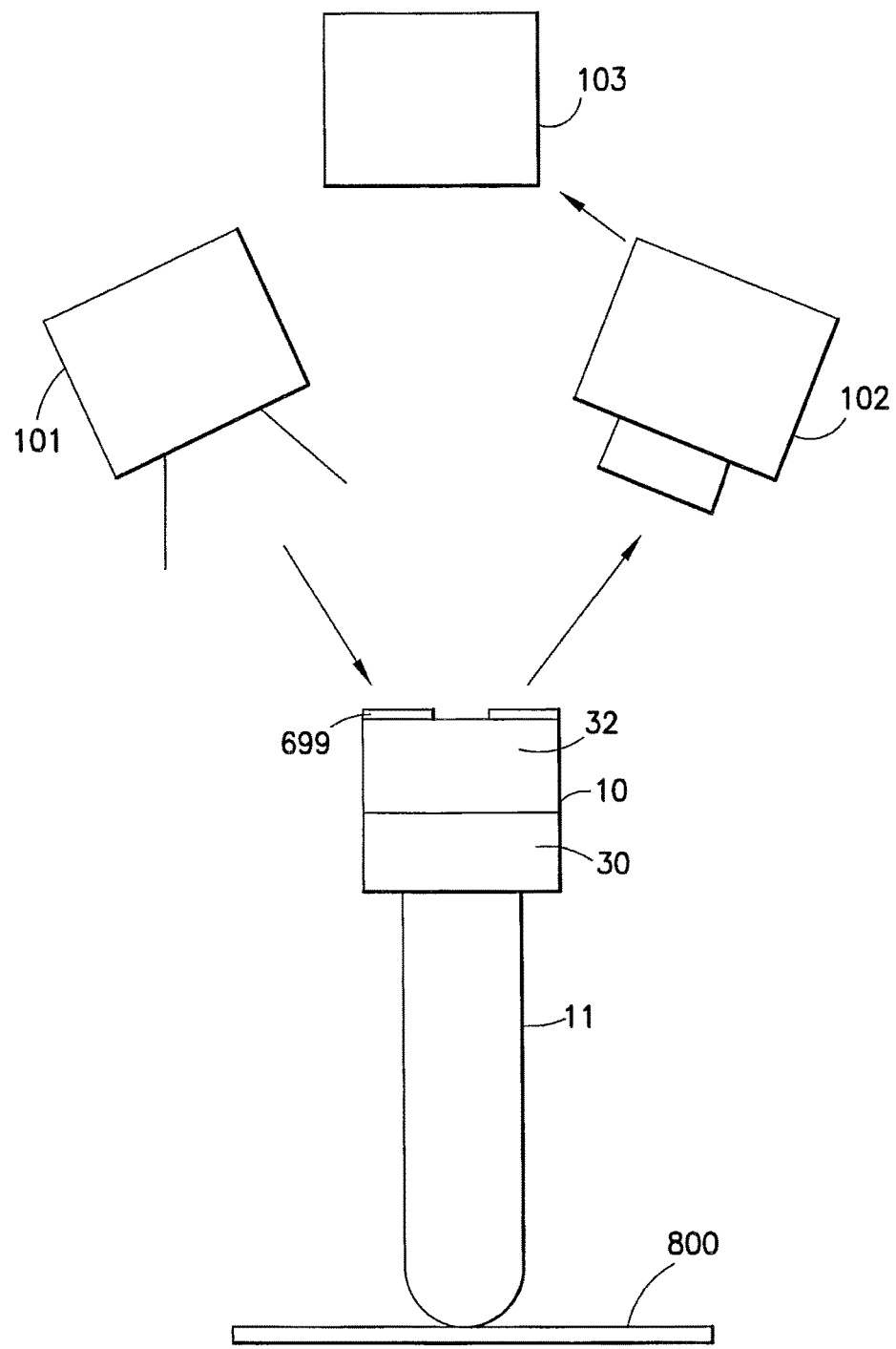
FIG. 58 is a side schematic view of a fluorescence detection station in accordance with an embodiment of the present invention.

Referring to FIG. 58, an automated process system may be utilized to identify the visual identifier(s) of the present invention for the purpose of identifying a feature of the sample collection container 11. In one embodiment, the closure 10 and sample collection container 11 may be provided in front of a background 800, such as a white background or a dark background 700, as described herein. A viewer 101, such as an ultraviolet light source, images the closure 10 and sample collection container 11, and a detector 102 views the visual identifier(s) to determine the contents of the sample collection container 11 and/or the intended testing procedure to be performed on the contents of the sample collection container 11 based on the visual identifier(s) 30, 32, 699. Depending on the information determined by the visual identifier(s) 30, 32, 699, the sample collection container 11 is routed to an appropriate processing step 103.

In one embodiment, if the visual identifier is a fluorescent compound, the detection of a fluorescence signal by the detector 102 may indicate that the sample collection container 11 is a blood collection tube. The fluorescence can be detected or measured by methods known in the art. Typically, the detection station communicates with a viewer having a light source, such as an ultraviolet light source 101 for emitting light onto the sample collection container 11. The viewer and light source 101 may emit light of a wavelength and intensity sufficient to cause the one or more fluorescent compounds to fluoresce at detectable levels, and detector 102 collects light produced by the fluorescence of the fluorescent compounds and converts the collected light into an analog or digital signal indicative of the intensity of the fluorescence of the coating. In one embodiment, the viewer and light source 101 and the detector 102 can be housed together in a probe head.

The light source 101 may emit electromagnetic radiation in the ultraviolet spectral regions. In one embodiment, the light source 101 is an ultraviolet lamp or black light filtered optically such that only those emissions lines between 250 and 400 nm are incident upon an illuminated sample. Alternative light sources may include, but are not limited to, xenon lamps, deuterium lamps, hollow cathode lamps, tungsten lamps, ion lasers, solid state lasers, diode lasers, and light emitting diodes. In one embodiment, the energy or energy range of the light source used is coincident with that of one or more electronic absorption bands of the fluorescing agent incorporated into or onto the tube, but not coincident with that of the fluorescence emission of the same fluorescing agent.

In a further embodiment, the detector 102 collects light produced by the fluorescence of the one or more fluorescent compounds and converts the collected light into an analog or digital electrical signal indicative of the intensity of the fluorescence of the coating. The detector 102 may contain optics for the collection and spectral filtering of light that is reflected by and emitted by a tube following illumination with light from the aforementioned light source. In one embodiment, spectral filtering optics reject light of energy or energy range coincident with that of the light source, while transferring, to the optical fiber, light of energy or energy range coincident with the fluorescence emission of the one or more fluorescent compounds on the sample collection container 11 and/or closure 10. It is contemplated herein that those skilled in the art can define geometric orientations for the excitation and emission light paths, such that excitation light cannot enter the emission light detection pathway. The detector unit can include any means known to one skilled in the art to isolate and measure electromagnetic radiation of an energy or energy range coincident with that of the fluorescence emission of the one or more fluorescent compounds on the tube. One embodiment of the detector is a light sensor or spectrograph, possibly including a monochromator or filter and a typical photomultiplier, photodiode array, and optionally a CCD camera system. The light exiting the optical fiber enters the monochromator and is dispersed by energy using a grating and then is either detected or "imaged" by the detector, resulting in a scorable electrical or digital signal.

Thus according to one embodiment of the present invention a blood collection tube 11 with a fluorescent compound molded into the shield of the closure 10 is used to obtain a sample of blood. The tube 11, and sample therein, is then loaded onto an automated sample transport mechanism which conveys the tube to a fluorescent detection station. The ultraviolet light source 101 then illuminates the tube. The detector then detects a fluorescent signal of a predetermined minimum intensity, (from the fluorescent compound molded into the shield) thereby confirming the existence of closure 10 on the tube 11. A processor (not shown) connected to the detector 102 then sends a signal to a processing system 103, such as an automatic decapper, to activate and remove the closure 10 from the tube 11. Therefore, in one embodiment, the fluorescent detection system of the present invention functions independently of, or in conjunction with, the color of the closure 10 and tube 11.

In another embodiment of the present invention, a particular fluorescent compound or combination of fluorescent compounds having a characteristic fluorescent spectrum can be selected to represent a particular type of blood collection tube. A spectral analyzer can be added to the detector which allows qualitative identification of the tube type via the characteristic fluorescent spectrum thus allowing a greater degree of automated control over various subsequent stages of the sample handling, preparation, and analysis processes according to the tube type. Spectral analysis may alternatively come directly from the imaged colors in a color-sensitive CCD system.

In a further embodiment of the invention, the closure or tube recognition can be applied in the assembly process of the blood collection tube. For example a fluorescent compound can be molded into or applied to the surface of a portion of the assembly such as the stopper or septum. The presence of a stopper or septum within the subassembly of the closure can then be confirmed by a detection station prior to each stage of the assembly process. Additionally, the degree of presence of a stopper or septum within the subassembly of the closure can be confirmed by a detection station. For example, the process can inspect for complete filling of the stopper or septum cavity by the molding process, thereby eliminating incomplete sealing closure systems, wherein the stopper or septum is with voids, partially incomplete, non-existent or not-present, and the like.

An additional embodiment of the invention includes a method for identifying a co-molded closure by providing a blood collection tube having a closure comprising a cap and a septum, wherein the shield or septum contains one or more fluorescent compounds that have characteristic fluorescent spectra, then placing the closure in a fluorescence detection station comprising an ultraviolet light source and a detector, illuminating the closure with ultraviolet light from the light source, measuring the fluorescent spectra of the one or more fluorescent compounds in either of the cap or septum, and identifying a septum/cap interface.

An Infra-Red (IR) based coloration system may be used instead of the combination of fluorescence and ultraviolet light such that the closure contains or is coated with an IR ink having an up-converting phosphor that is invisible in ambient light and becomes visible when excited by a concentrated or diffused IR light source.

The foregoing description is intended to be exemplary of a preferred embodiment of the invention. It will be understood by those skilled in the art that various changes and modifications to the disclosed embodiment can be made without departing from the purview and spirit of the invention as defined in the appended claims.

What is claimed is:

1. A device for collecting a biological sample, comprising:
   a patient sample collection container having a first end, a second end, and a sidewall extending therebetween;
   at least one closure for sealing at least one of the first end and the second end, the closure having a top portion and an annular skirt portion; and
   a first predefined visual identifier comprising a first fluorescent compound, wherein the first fluorescent compound is provided on the top portion of the closure, and a second predefined visual identifier is provided on the annular skirt portion of the closure, wherein the second visual identifier is formed from either a contrasting second fluorescent compound which is different than the first fluorescent compound or from a contrasting non-fluorescent material,
   wherein said second visual identifier is delineated from and visually discernable from the first visual identifier and wherein said first and second visual identifiers are co-molded with the at least one closure.

2. The device of claim 1, wherein a first part of the closure comprises a stopper and a second part of the closure comprises a shield.

3. The device of claim 1, wherein a first part of the closure comprises a cap and a second part of the closure comprises a septum.

4. The device of claim 1, wherein the sidewall of the collection container defines an interior volume and the first portion of the closure is positioned within the interior volume.

5. The device of claim 1, wherein the sidewall of the collection container defines an interior volume and the first portion of the closure is positioned outside of the interior volume.

\* \* \* \* \*